US008971600B2

(12) United States Patent
Yoshikawa et al.

(10) Patent No.: US 8,971,600 B2
(45) Date of Patent: Mar. 3, 2015

(54) ULTRASONIC DIAGNOSIS APPARATUS AND METHOD FOR CONSTRUCTING DISTRIBUTION IMAGE OF BLOOD FLOW DYNAMIC STATE

(75) Inventors: Hideki Yoshikawa, Hino (JP); Takashi Azuma, Sagamihara (JP)

(73) Assignee: Hitachi Medical Corporation, Tokyo (JP)

( * ) Notice: Subject to any disclaimer, the term of this patent is extended or adjusted under 35 U.S.C. 154(b) by 645 days.

(21) Appl. No.: 13/263,184

(22) PCT Filed: Apr. 7, 2010

(86) PCT No.: PCT/JP2010/056329
§ 371 (c)(1),
(2), (4) Date: Oct. 6, 2011

(87) PCT Pub. No.: WO2010/117025
PCT Pub. Date: Oct. 14, 2010

(65) Prior Publication Data
US 2012/0027282 A1    Feb. 2, 2012

(30) Foreign Application Priority Data
Apr. 10, 2009    (JP) .................................. 2009-095535

(51) Int. Cl.
*G06K 9/00* (2006.01)
*G06T 7/00* (2006.01)
(Continued)

(52) U.S. Cl.
CPC .............. *G01S 15/8979* (2013.01); *A61B 8/06* (2013.01); *A61B 8/13* (2013.01); *A61B 8/463* (2013.01);
(Continued)

(58) Field of Classification Search
CPC ................ G06T 7/0012; G06T 7/0016; G06T 2207/30104; G06T 2207/10132; G06T 2207/10136; A61B 8/06; A61B 8/46; A61B 8/461; A61B 8/469; A61B 5/026; A61B 5/0263
USPC .......... 382/134, 128; 600/309, 322, 334, 363, 600/407, 437, 454
See application file for complete search history.

(56) References Cited

U.S. PATENT DOCUMENTS
4,932,415 A  *  6/1990  Angelsen et al. ............. 600/455
5,170,792 A  *  12/1992  Sturgill et al. ................ 600/455
(Continued)

FOREIGN PATENT DOCUMENTS
CN    1593348 A    3/2005
(Continued)

OTHER PUBLICATIONS
International Search Report and Written Opinion for PCT International Application No. PCT/JP2010/056329, mailed May 25, 2010.

*Primary Examiner* — Michael A Newman
(74) *Attorney, Agent, or Firm* — Brundidge & Stanger, P.C.

(57) ABSTRACT

An ultrasonic diagnostic apparatus is provided for displaying a color map on which a difference in blood flow dynamics is reflected. Setting a test subject who is administered a contrast agent is assumed as an imaging target, and a probe transmits and receives ultrasonic waves to and from the target for contrast imaging. Image data is constructed based on signals received by the probe and a time-intensity curve is generated from intensity values of the image data. According to the time-intensity curve, a value of a predetermined parameter is calculated for producing a distribution image of blood flow dynamics. The distribution image (color map) of the blood flow dynamics is produced from the parameter value. The color map is a two-dimensional or a three-dimensional image being color-coded according to the parameter value. At least one of the followings may be used as the parameter; a contrast agent inflow start time, a balanced intensity arrival time, a contrast agent disappearance start time, a contrast agent duration, a preset threshold arrival time, an intensity increase rate, an intensity decrease rate, intensity of balanced state, and a total flow amount.

17 Claims, 23 Drawing Sheets

(51) Int. Cl.
*A61B 8/00* (2006.01)
*G01S 15/89* (2006.01)
*A61B 8/06* (2006.01)
*A61B 8/13* (2006.01)
*A61B 8/08* (2006.01)
*G01S 7/52* (2006.01)

(52) U.S. Cl.
CPC ............... *A61B 8/469* (2013.01); *A61B 8/481* (2013.01); *A61B 8/483* (2013.01); *G01S 15/8993* (2013.01); *G01S 7/52071* (2013.01)
USPC ........... 382/128; 382/134; 600/309; 600/322; 600/334; 600/363; 600/407; 600/437; 600/454

(56) References Cited

U.S. PATENT DOCUMENTS

| | | | |
|---|---|---|---|
| 5,255,683 A * | 10/1993 | Monaghan | 600/458 |
| 5,471,990 A | 12/1995 | Thirsk | |
| 5,615,680 A * | 4/1997 | Sano | 600/437 |
| 5,910,119 A * | 6/1999 | Lin | 600/455 |
| 6,436,049 B1 | 8/2002 | Kamiyama et al. | |
| 6,582,370 B2 * | 6/2003 | Jibiki | 600/455 |
| 6,659,953 B1 | 12/2003 | Sumanaweera et al. | |
| 7,972,269 B2 * | 7/2011 | Hayashi et al. | 600/443 |
| 8,460,192 B2 * | 6/2013 | Yoshiara et al. | 600/437 |
| 2002/0103437 A1 * | 8/2002 | Jibiki | 600/454 |
| 2005/0059893 A1 * | 3/2005 | Ogasawara et al. | 600/454 |
| 2008/0200808 A1 * | 8/2008 | Leidel et al. | 600/443 |
| 2009/0005683 A1 | 1/2009 | Hashimoto et al. | |

FOREIGN PATENT DOCUMENTS

| | | |
|---|---|---|
| EP | 1514516 A1 | 3/2005 |
| JP | 06189956 | 7/1994 |
| JP | 08224238 | 9/1996 |
| JP | 09-024047 | 1/1997 |
| JP | 10-305035 | 11/1998 |
| JP | 11-000327 | 1/1999 |
| JP | 2000 333956 A | 5/2000 |
| JP | 2001-269341 | 10/2001 |
| JP | 2002-165795 | 6/2002 |
| JP | 2003-061959 | 3/2003 |
| JP | 2004 000620 | 1/2004 |
| JP | 2005-081073 | 3/2005 |
| JP | 2005 081073 A | 3/2005 |
| JP | 2005-137574 | 6/2005 |
| JP | 2006-055672 | 3/2006 |
| JP | 2008-086767 | 4/2008 |
| JP | 2009 005755 | 1/2009 |
| JP | 4408988 B2 | 3/2010 |

* cited by examiner

ULTRASONIC DIAGNOSIS APPARATUS AND METHOD FOR CONSTRUCTING DISTRIBUTION IMAGE OF BLOOD FLOW DYNAMIC STATE

TECHNICAL FIELD

The present invention relates to a technique which transmits an ultrasonic wave directed inside a living body and performs imaging of information inside the living body according to a signal being received, and more particularly, it relates to an ultrasonic diagnostic apparatus for calculating information as to a bloodstream based on an image taken by using a contrast agent, and creating a picture to be displayed.

BACKGROUND ART

An ultrasonic diagnostic apparatus is a type of imaging apparatus generally employed in a medical field, together with an MRI system and a CT scanner, and characterized by compact in size, a high spatial and time resolution, and the like. In recent years, along with the widespread use of ultrasonic contrast agent, a vessel imaging technique and a tumor imaging technique have been developed, and therefore, expectations are rising for improved diagnostic performance.

The bloodstream around a tumor or inside the tumor indicates not only whether any lesion exists, but also properties of its tissue, and provides significant information for a differential diagnosis. Previously, CTA (CT-Angiography) which uses X-rays has been the mainstream of the method for acquiring an image of vessels. In the CTA, an iodine contrast agent is intravenously injected, and a plurality of X-ray images are reconstructed, each of the images being acquired during a passage of the contrast agent through blood vessels, thereby allowing a vascular structure to be three-dimensionally visualized. On the other hand, the CTA sometimes places a load on a patient, due to exposure to X-rays and administration of the contrast agent.

Compared with this, ultrasonic diagnostic imaging is not attended with invasion such as exposure to X-rays when imaging is performed. In addition, since micro bubbles, a few micrometers in diameter, are used as the contrast agent, the contrast agent itself does not possess any toxicity. Such micro bubbles are discharged from the body as time advances, by a natural metabolic function in the body. Therefore, the ultrasonic imaging diagnosis has a characteristic that a burden placed on the patient is small. The micro bubbles (ultrasonic contrast agent) issues strong nonlinear signals, in sympathetic vibration with a few MHz ultrasonic waves used in a medical field. Therefore, it is possible to detect these nonlinear signals specifically to create a picture, thereby visualizing a microscopic vascular structure as a high-contrast image.

The ultrasonic contrast agent is roughly classified into a high sound pressure type and a low sound pressure type, according to a difference in behavior against ultrasonic irradiation. As for the high sound pressure type agent, air bubbles are collapsed by applying pressure under ultrasonic irradiation of high sound pressure (mechanical index: MI from 1.0 to 1.9), and nonlinear signals generated at this time produce an image. Since the contrast agent (micro bubbles) disappears every irradiation, it is necessary to change an imaging plane appropriately in order to observe a contrast image of an identical region. On the other hand, as for the low sound pressure type (MI from 0.1 to 0.9), an image is produced by nonlinear signals which are obtained by establishing resonance under the ultrasonic irradiation, without collapsing the air bubbles by applying pressure. Therefore, a persistent contrast imaging effect is produced, thereby allowing continuous observation of the identical region. In addition, a part of the contrast agent (micro bubbles) is subjected to Kupffer cell phagocyte function, the cells existing in the sinusoid connecting the artery and the portal vein, with the central vein. Therefore, if the ultrasonic irradiation is applied in the state where the liver tissue is filled with the contrast agent, a region where the Kupffer cells are normally functioning is enhanced at high intensity, and it is possible to identify an area of lesion, such as tumor, according to a defect of intensity. Furthermore, an intensity level or duration of contrast enhancement serves as an index for evaluating the function of the Kupffer cells. Therefore, such information items are also considered to be effective for functional diagnosis of the liver.

A contrast image using ultrasonic waves as described above is effective not only for observing the microscopic vascular structure, but also for determining a function of tissue, and it is getting to be used widely, with a focus on an abdominal region.

There is further an advantage that the low sound pressure type contrast agent as described above issues nonlinear signals according to resonance caused by ultrasonic irradiation, and maintains a contrast effect, therefore allowing observation of the contrast enhancement progress in an identical imaging plane.

A process of the contrast enhancement using the ultrasonic contrast agent is different by the types of tissue. For example, in the case of a normal liver, each vessel of artery, portal vein, and vein is enhanced in a different time phase, according to a difference of its neural path, and thereafter, the enhancement of the tissue is performed. However, if a tumor exists, the process of enhancement is different depending on the degree of vascular proliferation or activation. Therefore, by observing dynamics of the enhancement in detail, it is possible to know an aspect of the tumor. Such difference in the enhancement process depending on the tissue indicates a bloodstream variation, i.e., blood flow dynamics, such as a flow passage, a flow amount, and a flow rate of the bloodstream originating from a heart.

Time-Intensity Curve (TIC) serves as a significant index in quantifying a difference in the process of enhancement. This is obtained by plotting intensity change per time unit along with an inflow of the contrast agent. For example, in the case of a liver tumor, it is important to know in discrimination, which is the starting point to form a tumor vessel, from the artery or from the portal vein. However, since the artery runs in parallel with the portal vein, once the enhancement begins in the portal vein, it is difficult to discriminate the portal vein from the artery, by viewing a just single contrast image. However, by comparing the TICs of the respective vessels, a difference in the process of enhancement can be evaluated, and it is possible to objectively determine which vessel is the starting point of the tumor vessel.

The Patent Document 1 describes a technique which calculates an index value such as a mean intensity value, from the TICs measured by a wave transmission sequence where high and low sound pressures are combined, and displays an image which is color-coded according to the calculated value. Ultrasonic irradiation under high sound pressure against the tissue filled with a contrast agent triggers a start of the TIC measurement, and subsequently, the measurement is conducted as to a process of enhancement of the contrast agent with which the imaging plane is reperfused, by the irradiation under low sound pressure.

PRIOR ART DOCUMENT

Patent Document

[Patent Document 1]
Japanese Unexamined Patent Application Publication No. 2005-81073

DISCLOSURE OF THE INVENTION

Problem to be Solved by the Invention

However, according to the aforementioned conventional technique, it is necessary to visually observe a moving picture, which is being reproduced repeatedly, in order to compare blood flow dynamics with respect to each area. Therefore, the conventional technique has some problems as the following; the information is less objective, multiple areas cannot be observed simultaneously, it is burdensome for an operator, and the like. In addition, it is significant to observe the blood flow dynamics starting from a heart in order to evaluate a tissue aspect. Therefore, it is necessary to observe a passage of enhancement, from the point when the contrast agent being administered flows with original blood perfusion and reaches the tissue.

An object of the present invention is to provide an ultrasonic diagnostic apparatus which employs the TIC indicating enhancement change per time unit, from the time when a contrast agent is administered until reaching the tissue enhancement, calculates a value of an evaluation index indicating the blood flow dynamics starting from the heart, and produces a color map according to the value of the evaluation index.

Means to Solve the Problem

According to the present invention, there is provided an ultrasonic diagnostic apparatus as the following. That is, the ultrasonic diagnostic apparatus includes a probe for transmitting and receiving ultrasonic waves to and from an imaging target, an image data construction unit for constructing image data based on signals received by the probe, a time-intensity curve calculation unit for generating a time-intensity curve from an intensity value of the image data, a distribution image producing unit for producing a distribution image of blood flow dynamics based on a value of a predetermined parameter obtained from the time-intensity curve, and a display unit for displaying the distribution image of the blood flow dynamics.

Effect of the Invention

According to the present invention, it is possible to evaluate the blood flow dynamics starting from the heart by using the time-intensity curve (TIC), and display in color, an image representing variations in vessels and tissue aspects, thereby providing an image display apparatus which facilitates a comparison of variations in the blood flow dynamics.

BRIEF DESCRIPTION OF THE DRAWINGS

FIG. 4($b$) is a graph showing the TIC generated in the step 102, and FIG. 4($c$) is a graph showing the TIC that is obtained by smoothing the TIC generated in the step 102;

FIG. 7($b$) illustrates coordinates of the structural object 211 and coordinates of the TIC acquiring position (pixel) 212 in the case where the TIC is generated after the position adjustment process is performed, and FIG. 7($c$) illustrates coordinates of the TIC acquiring position (pixel) both in the case where the position adjustment process is performed and in the case where it is not performed;

DESCRIPTION OF THE PREFERRED EMBODIMENTS

First Embodiment

Hereinafter, preferred embodiments of the present invention will be explained with reference to the accompanying drawings.

Figure 1:
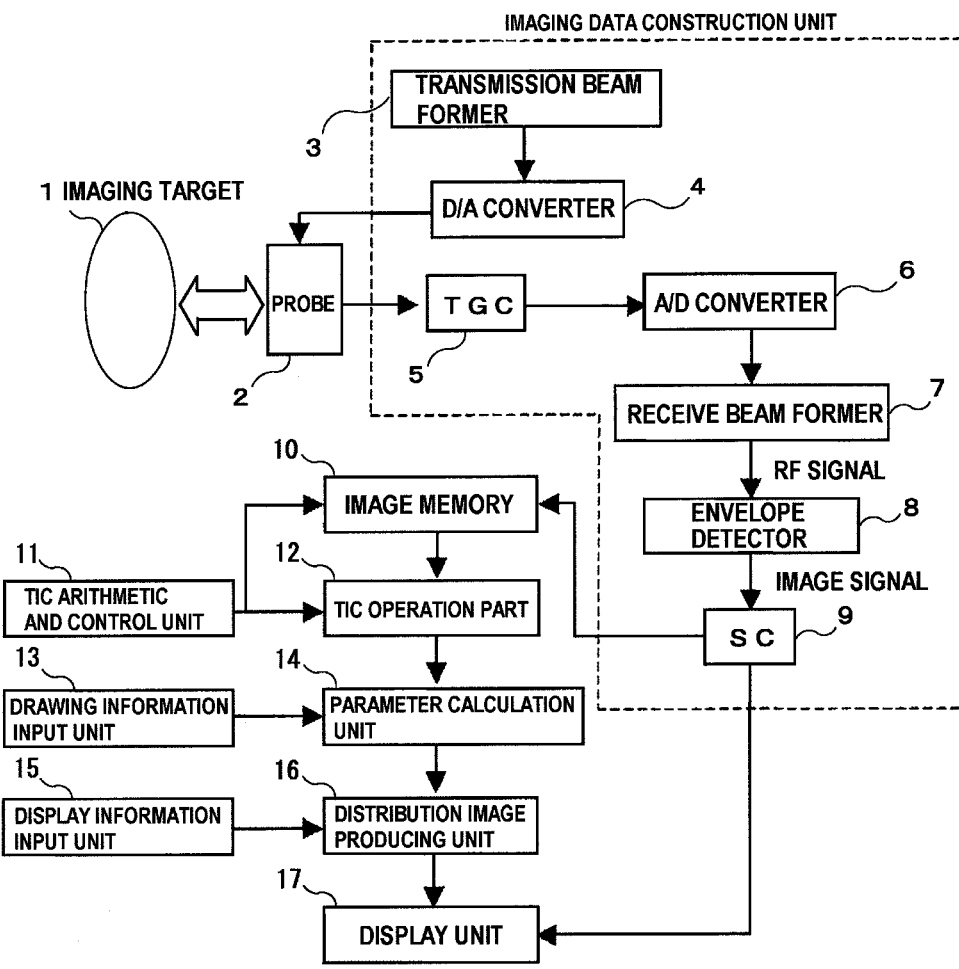
FIG. 1 is a block diagram showing a configuration example of an ultrasonic diagnostic apparatus according to a first embodiment.

FIG. 1 is a block diagram showing the ultrasonic diagnostic apparatus (image display apparatus) according to the first embodiment.

This apparatus includes, a probe 2 for transmitting and sending ultrasonic signals to and from an imaging target 1, a transmission beam former 3 and a receive beam former 7 for providing a predetermined time delay to form desired transmission and receiving beams on piezoelectric elements constituting the probe 2, a D/A converter 4 for converting a transmitted signal from digital to analog, an A/D converter 6 for converting a received signal from analog to digital, a TGC (time gain controller) 5 for compensating for amplitude attenuation that occurs in the course of propagation of ultrasonic signals inside a living body, an envelope detector 8 for detecting a received RF (radio frequency) signal and converting the signal into an image signal, a SC (scan converter) 9 for constructing two-dimensional image data from the image signal, an image memory 10 for storing the image data at a predetermined sampling interval being constructed by the SC 9, a time intensity curve (hereinafter, referred to as "TIC") arithmetic and control unit 11 for performing a control relating to the TIC generation, such as setting of the sampling interval of the image data and a region of interest for generating the TIC, a TIC operation part 12 for generating the TIC based on control details set in the TIC arithmetic and control unit 11, a drawing information input unit 13 for designating an evaluation index (parameter) calculated from the TIC, a parameter calculation unit 14 for calculating a value of the parameter designated in the drawing information input unit 13, from the TIC generated by the TIC operation part 12, a distribution image producing unit 16 for producing a color map based on the value of the parameter being calculated, a display unit 17 for displaying an image produced by the distribution image producing unit 16, and a display information input unit 15 for accepting a change of display mode of the color map and the TIC, being displayed on the display unit 17.

As shown in FIG. 1, a system from receiving a signal via the probe 2 until constructing image data is referred to as a data construction unit. The image constructed in the image data construction unit corresponds to a monochrome image (B-mode) or an image using a contrast agent (an image where signals from the contrast agent are enhanced according to a sequence of transmission and receiving, a filter processing, or the like), such images being generated by generally used medical ultrasound equipment. A method for constructing the image is generally known, and a brief explanation will be given here. A surface of the probe 2 used for emitting ultrasonic waves has a configuration of one-dimensional array where multiple piezoelectric elements are arranged in one line, and each element has functions for transmitting and receiving ultrasonic waves. A voltage pulse from the transmission beam former 3 is inputted in each of the piezoelectric elements via the D/A converter 4, and piezoelectric vibration of the elements irradiates the imaging target 1 with ultrasonic waves. On this occasion, a predetermined time delay is electronically given to each of the piezoelectric elements, and the ultrasonic waves transmitted respectively from the piezoelectric elements are brought into focus at a predetermined position inside the imaging target 1. Reflection echoes from the imaging target 1 are received by each of the piezoelectric elements, and the reflection echoes are subjected to amplitude compensation in the TGC 5 depending on a propagation distance, in order to compensate for a signal attenuation which is given during the propagation process. Subsequently, the received signals are transmitted to the receive beam former 7 via the A/D converter 6, multiplied by a delay time depending on the distance from the focal point to each of the piezoelectric elements, and a result of addition is outputted (phasing and adding process).

As a method for enhancing the signals from the contrast agent and producing an image, there is a well-known method, for example, that two signals having phases inverted to each other are transmitted, and the signals being received are added. Here, fundamental frequency components mainly associated with tissue components are suppressed by adding the received signals. On the other hand, higher harmonic components, mainly associated with signals from the contrast agent, are reinforced.

Transmission and receiving of ultrasonic waves are performed on all the scanning lines, along the line of the piezoelectric elements, thereby obtaining a two-dimensional distribution of reflection echoes of the imaging target 1. An RF signal divided into real part and imaginary part is outputted from the receive beam former 7, and this signal is transmitted to the envelope detector 8. The signal transmitted to the envelope detector 8 is converted into a video signal, thereafter, pixel interpolation between scan lines is performed by the SC 9, and then two-dimensional image data is reconstructed and displayed on the display unit 17.

Figure 2:
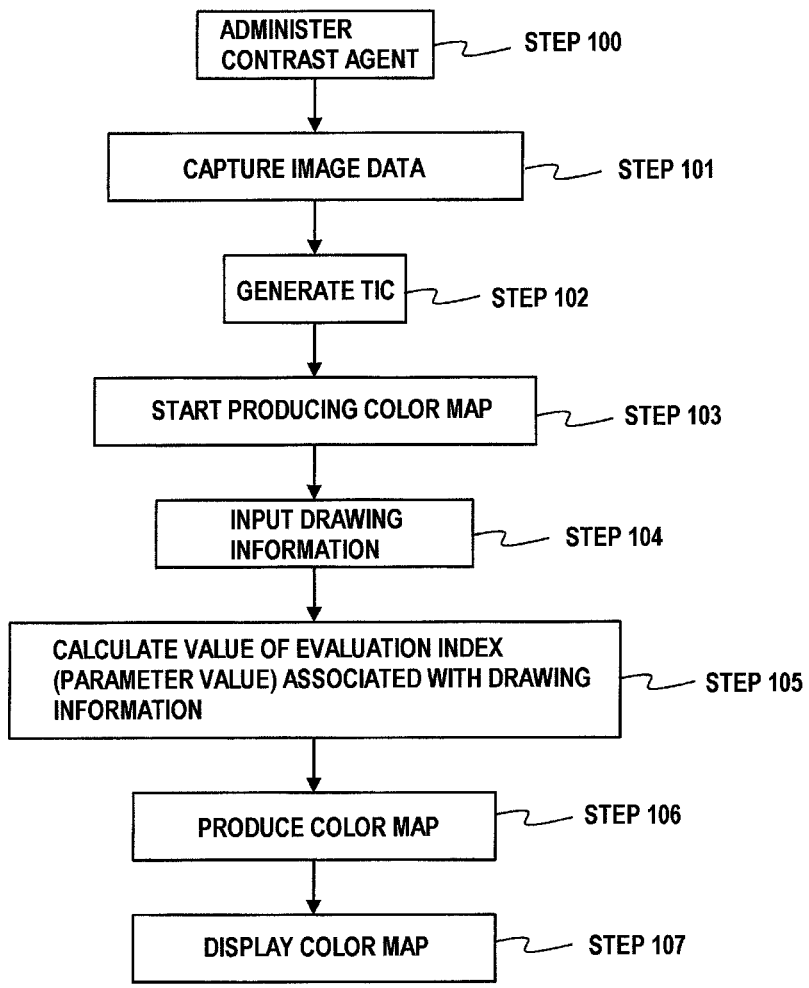
FIG. 2 is a flowchart showing processing steps from administration of a contrast agent to displaying a color map according to the first embodiment.

Next, according to the flowchart as shown in FIG. 2, there will be explained processing steps for generating the TIC with the use of the image data reconstructed by the SC 9, and for generating a color map on which the blood flow dynamics are reflected.

Figure 3:
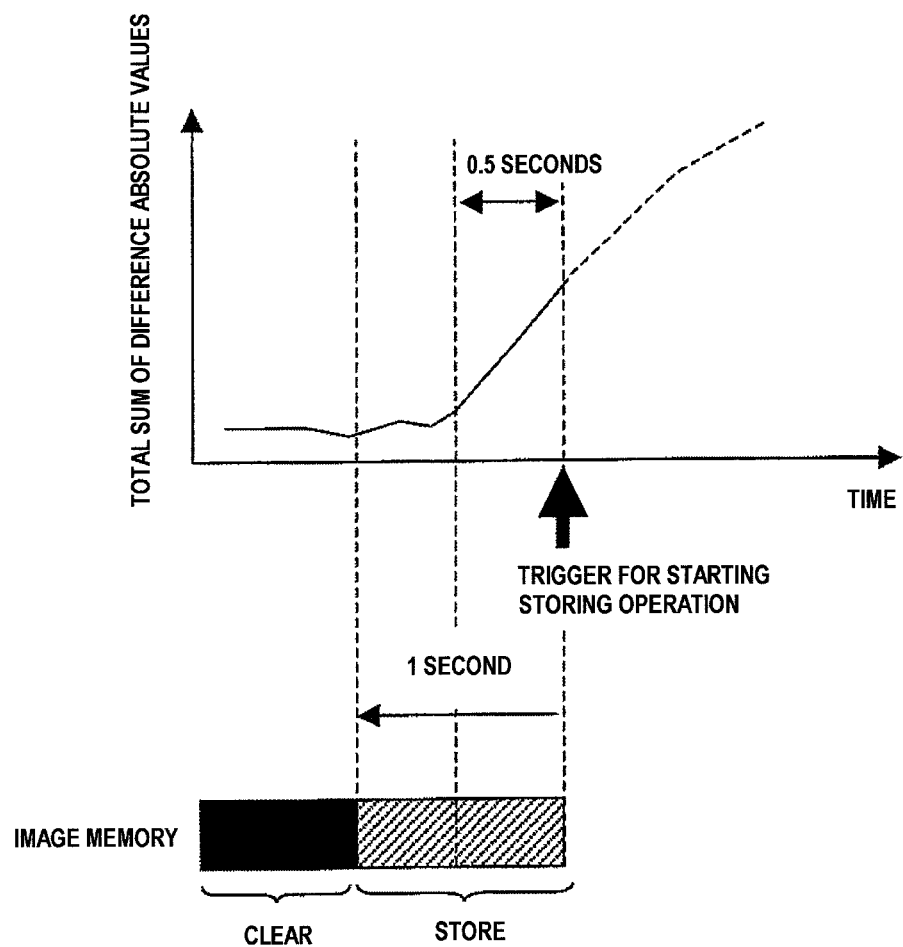
FIG. 3 illustrates a trigger for storing image data according to the first embodiment.

Firstly, an operator manipulates the probe 2 according to a general usage, checks the image data displayed on the display unit 17, and fixes a focused area as an imaging plane. Next, simultaneously with administering the contrast agent, the operator stores the image data in the image memory 10 (steps 100 and 101). If starting and terminating the storing operation are manually performed, the operator manipulates, for example, a switch provided on an operation panel of the ultrasonic diagnostic apparatus, thereby configuring in such a manner that a trigger to start storing the image data is inputted into the TIC operation part 12. The trigger signal is transmitted to the SC 9, and the storing process into the image memory 10 is started. If a TIC switch is provided on the probe 2, the operability is further enhanced. If starting the storing operation is automatically performed, for example, it is configured in such a manner that the image data being acquired and the image data acquired immediately before are compared, and the storing process is started automatically, from the time point when there is a major change in intensity therebetween. This configuration will further improve the operability. Specifically, difference values between pixels, respectively of the image being acquired and the image acquired immediately before, are calculated, and a total sum thereof is obtained. It is configured in such a manner that from the time when a value of the total sum keeps increasing for 0.5 seconds (corresponding to 10 frames when the frame rate is 20), storing of the image data is automatically started. Increase of intensity at the time of inflow of the contrast agent continues for a few seconds, and it takes one second or more as a time difference until when the contrast agent flows in the artery, portal vein, and the other vessels. Therefore, it is possible to obtain data on which the blood flow dynamics of each vessel are reflected, even though the image data is obtained after a lapse of 0.5 seconds, from the time point when the inflow is started as described above. It is further possible to configure as the following; a system is established where the image data being acquired is stored in advance, and from the time point when a trigger is entered to start storing the image data, manually by an operator or automatically, the image starting from only a predetermined number of seconds before (from one second to a few seconds) is retained and the image data before then is discarded, thereby allowing the data just before the contrast agent inflow to be stored (FIG. 3). On this occasion, the operator sets in advance in the TIC arithmetic and control unit 11, a sampling interval of the image data to be stored in the image memory 10. It is preferable to store the entire image data constructed by the SC 9 in order to generate a TIC (time intensity curve) at a high level of precision. However, if there is any restriction such as memory capacity, it is necessary to set the sampling interval considering the frame rate for acquiring the image data, so as to reduce the load on the memory. Since the intensity reaches the equilibrium state just after a few seconds of increasing along with the inflow of the contrast agent, sampling at approximately 4 Hz is necessary at least. Therefore, if the frame rate is 20 Hz, for example, the image data is stored every 5 frames.

Figure 4:
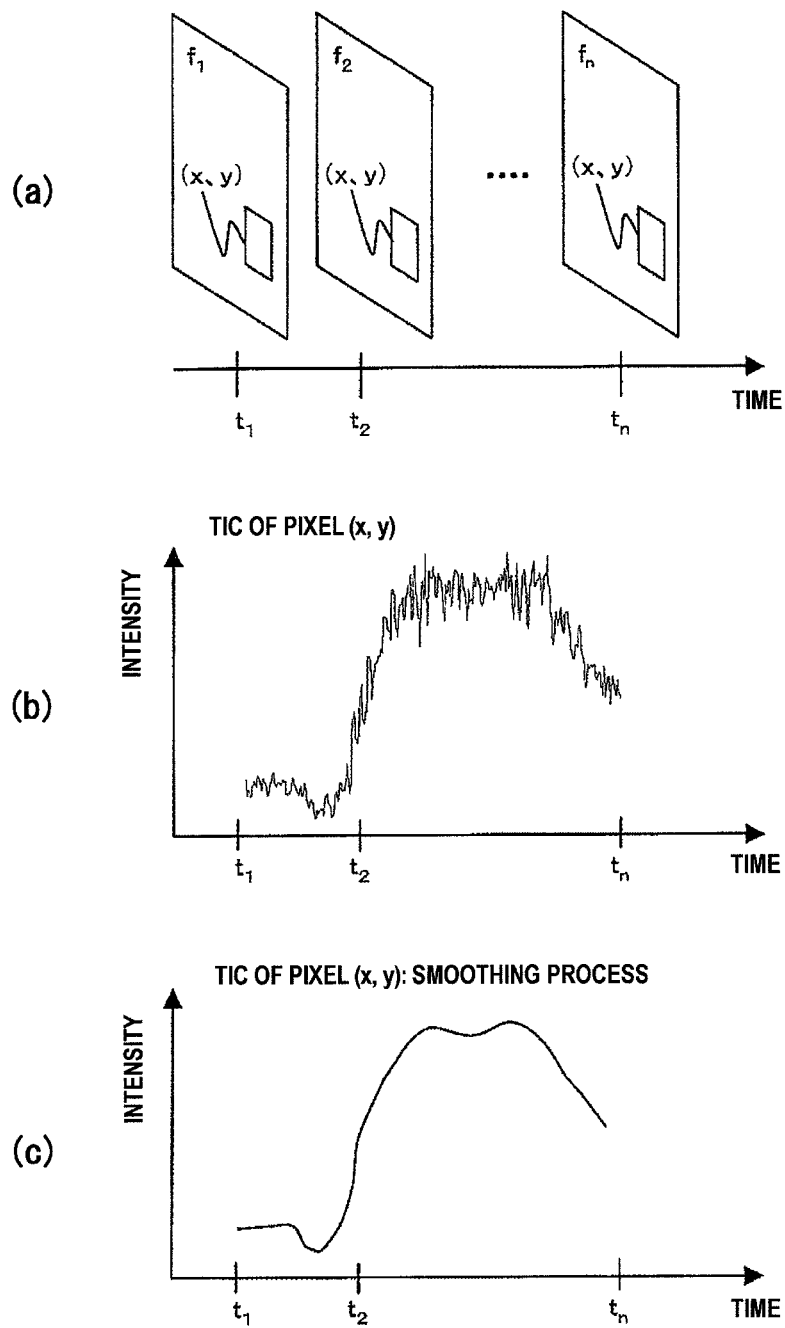
FIG. 4($a$) illustrates a process for acquiring intensity values of the same pixel of the image data in the step 102 according to the first embodiment.

In the step 102, as shown in FIG. 4(a), the TIC operation part 12 focuses attention on a single pixel (x, y) (x=1 ... $x_{max}$, y=1 ... $y_{max}$) constituting the image data (the image size is ($x_{max} \times y_{max}$)) stored in the image memory 10, and carries out operation for acquiring intensity values (f1(x, y), f2(x, y), ... fn(x, y)) of the pixel located at an identical position, from overall time-series image data being acquired. The time is set on the horizontal axis, the intensity value is set on the vertical axis, and the intensity values being acquired are plotted. Consequently, as shown in FIG. 4(b), the TIC of the pixel (x, y) is generated. Since variations of intensity before starting contrast radiography are important for the TIC, an initial value f1(x, y) is subtracted from each intensity value, and the intensity value zero is set as a starting point. It is to be noted that since the information of the initial value is maintained, the operator may optionally resume the original TIC for checking.

Generation of the TIC may be performed for all the pixels of the image data being stored in the image memory 10. Alternatively, a pixel range is set in advance, and the TIC of an average intensity value in the pixel range may be generated.

The pixel range for generating the TIC, that is, the range for constructing an image may be restricted to the extent within the region of interest, which the operator sets on the image data. As for the setting of the region of interest, it is possible to configure such that the operator performs the setting in advance on the image data displayed on the display unit 17, before starting the process for storing the image data. It is alternatively possible to configure such that after completing the storage of the image data, an appropriate image data item is made to be displayed on the display unit 17, being selected from the stored image data items, and the operator sets the region of interest on the selected image data. It is further possible that if the region of interest is set before starting the process for storing the image data, the image data itself to be stored in the image memory 10 may be restricted to the extent of the region of interest. In this case, the load on the memory may be reduced. The operator inputs in the TIC arithmetic and control unit 11, information of the region of interest which restricts the pixel range for generating the TIC.

Next, smoothing process is performed on the TIC being generated (FIG. 4(b)). The smoothing process is an averaging process performed in the time axis direction of the TIC, thereby reducing unevenness of intensity caused by displacements of pixels and effect of noise. Since the sampling points for generating the TIC are maintained, when averaging is carried out on five points, assuming the intensity values for each time ti (i=1, 2, ...) as $I_{ti}$, the intensity values at each time after the processing are calculated as $I_{t1}=(I_{t1}+I_{t2}+I_{t3}+I_{t4}+I_{t5})/5$ and $I_{t2}=(I_{t2}+I_{t3}+I_{t4}+I_{t5}+I_{t6})/5$. FIG. 4(c) illustrates the TIC after the smoothing process is performed.

The TIC generation process in the step 102 is executed simultaneously with storing the image data, except the case where setting the region of interest is performed on the image data being stored in the image memory 10.

Figure 5:
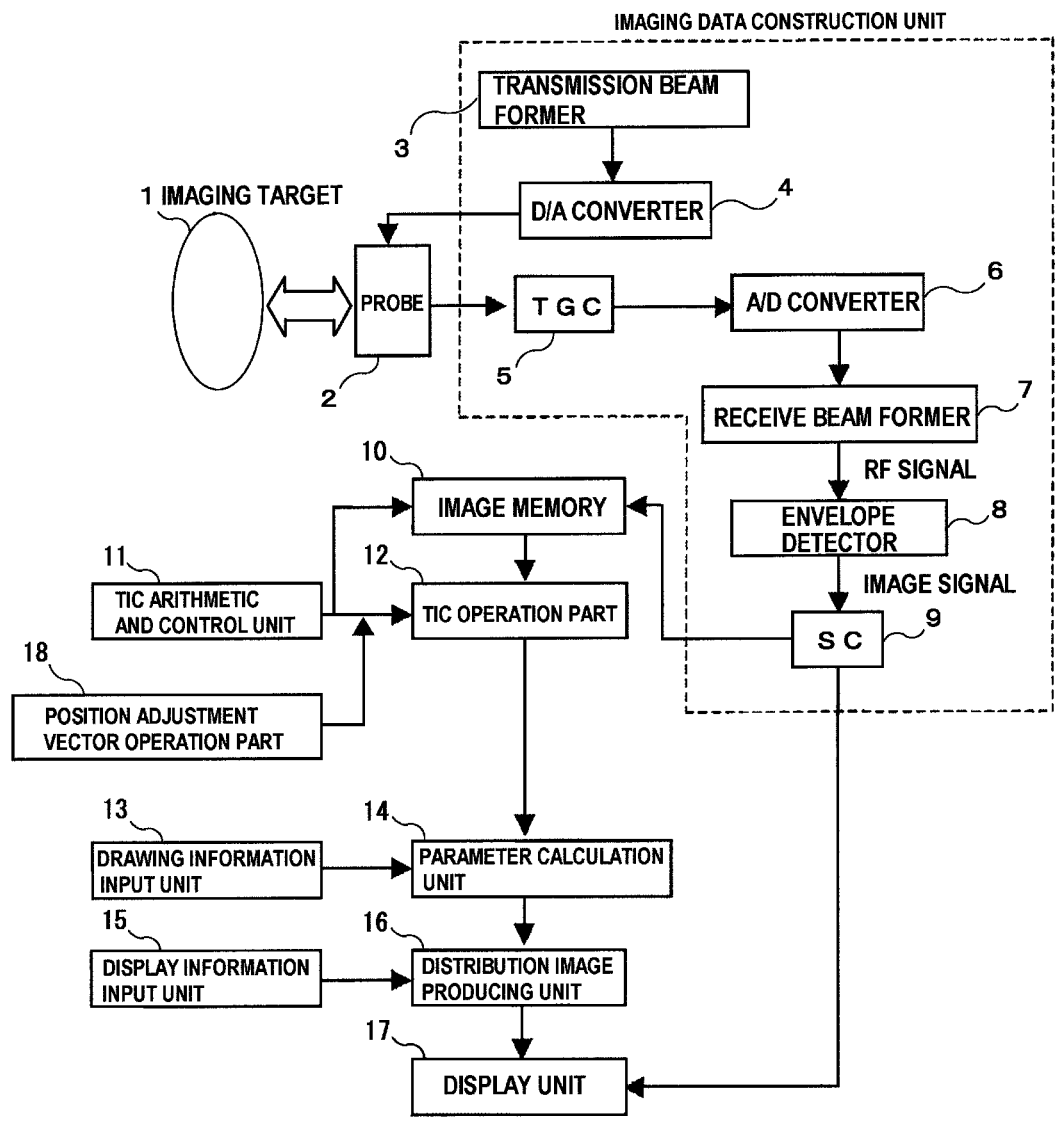
FIG. 5 is a block diagram showing a configuration example where a position adjustment vector operation part is provided in addition to the device configuration of the first embodiment.
Figure 6:
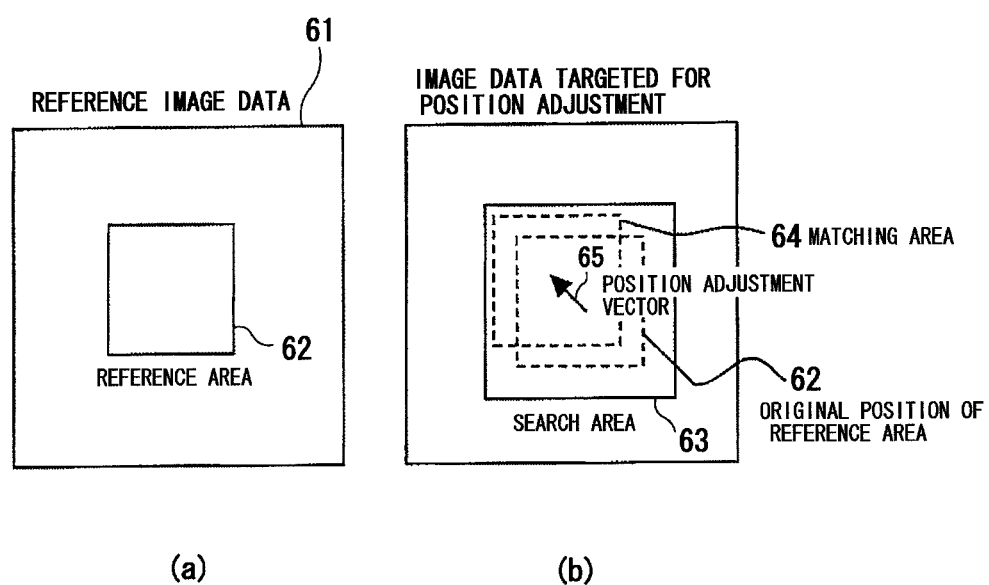
FIG. 6($a$) illustrates setting of a reference area in the image data in order to perform the position adjustment process in the first embodiment, and FIG. 6($b$) illustrates setting of a search area in the image data, in order to generate a position adjustment vector.
Figure 7:
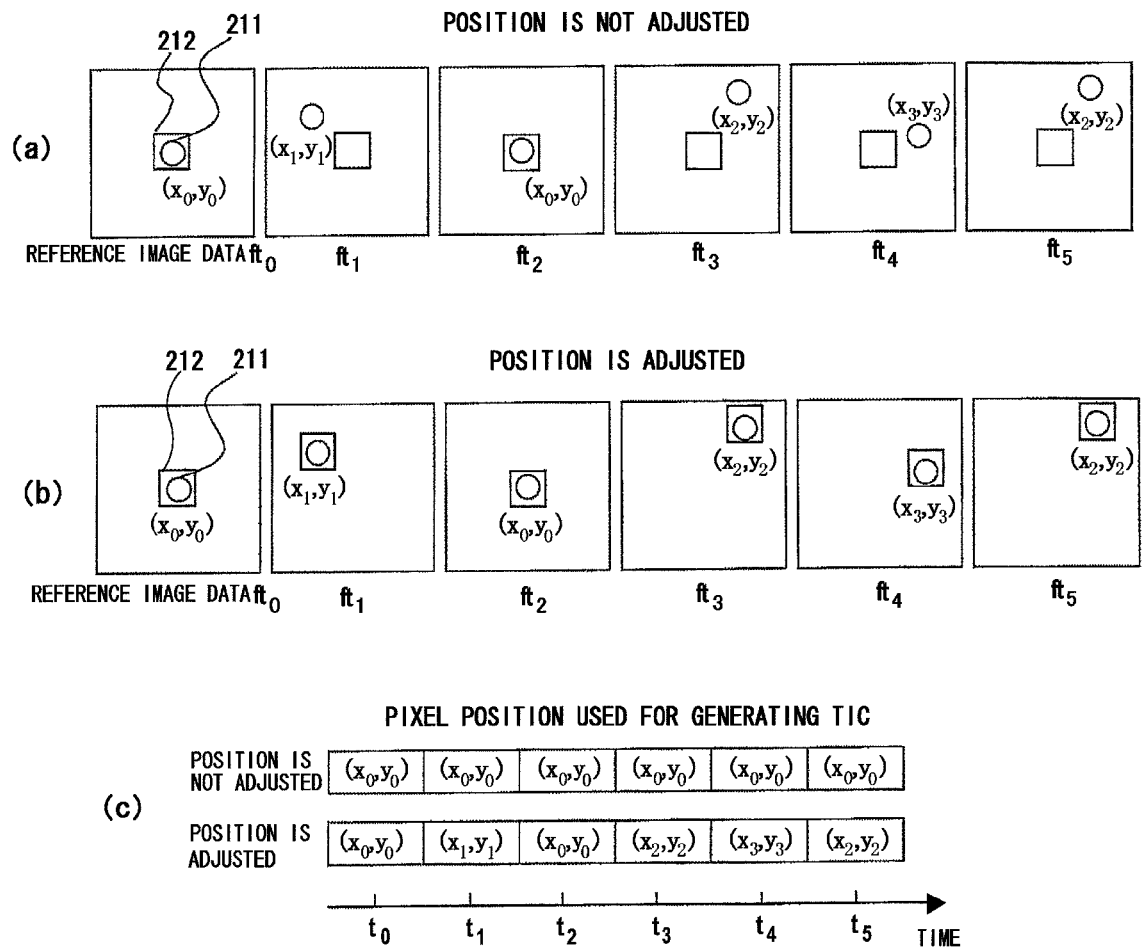
FIG. 7($a$) illustrates coordinates of a structural object 211 and coordinates of a TIC acquiring position (pixel) 212 in the case where the TIC is generated without the position adjustment process in the first embodiment.

If there is a large body motion or operator's hand motion, when the TIC operation part 12 generates a TIC, displacement of the imaging target occurs in the image data, and the TIC may be generated with errors. In order to compensate for the displacement, the apparatus is configured in such a manner as being provided with a position adjustment vector operation part 18 as shown in FIG. 5, and a position adjustment process is performed if necessary, as a previous step of the TIC generation process. A pattern matching process, generally known, is employed as the position adjustment process. Firstly, as shown in FIG. 6(a), a reference area 62 is placed as a reference of the position adjustment, on the first image data 61 being acquired. Next, as shown in FIG. 6(b), a search area 63 is set on the image data being a target for the position adjustment. The center position of the search area 63 corresponds to that of the reference area 62, and the operator optionally determines the size the search area, according to magnitude of displacement to be compensated for. A matching area 64 that can be assumed as identical to the reference area 62 is retrieved from the search area 63, and a vector connecting the center position of the matching area 64 and the center position of the search area 63 is generated as a position adjustment vector 65 (FIG. 6(b)). A method for retrieving the matching area 64 is as the following, for example; while the reference area 62 is displaced pixel by pixel within the search area 63, a total sum of difference absolute values is calculated, and when that absolute value becomes a minimum, the area is assumed as the matching area. A value used as an index for retrieval may be a least square sum, a correlation value of a cross-correlation operation, or the like, other than the total sum of difference absolute values as described above. Next, when an intensity value is read from each image data item being stored, the TIC operation part 12 adjusts the pixel position where the intensity value is read, according to the generated position adjustment vector 65, thereby reducing the influence caused by the displacement of the imaging target in generating the TIC. FIG. 7(a) illustrates reference image data $f_{t0}$, images ($f_{t1}$, $f_{t2}$, $f_{t3}$, $f_{t4}$, and $f_{t5}$) as targets for the position adjustment, a position of a structural object 211 in each of those images, a TIC acquisition position (pixel) 212, and position coordinates of the structural object 211 on each image data item. If there is no position adjustment being applied, the TIC acquisition position 212 is fixed regardless of any position change of the structural object 211 (FIG. 7(c)). Therefore, there occurs an error due to the displacement, since intensity value of the same pixel ($x_0$, $y_0$) is acquired. On the other hand, as shown in FIG. 7(b), if the TIC acquisition position 212 is shifted according to the position adjustment vector 65 (FIG. 6(b)), it is possible to coincide the coordinates of the structural object 211 with the coordinates of the TIC acquisition position 212 (FIG. 7(c)). This allows an accurate TIC generation.

Figure 8:
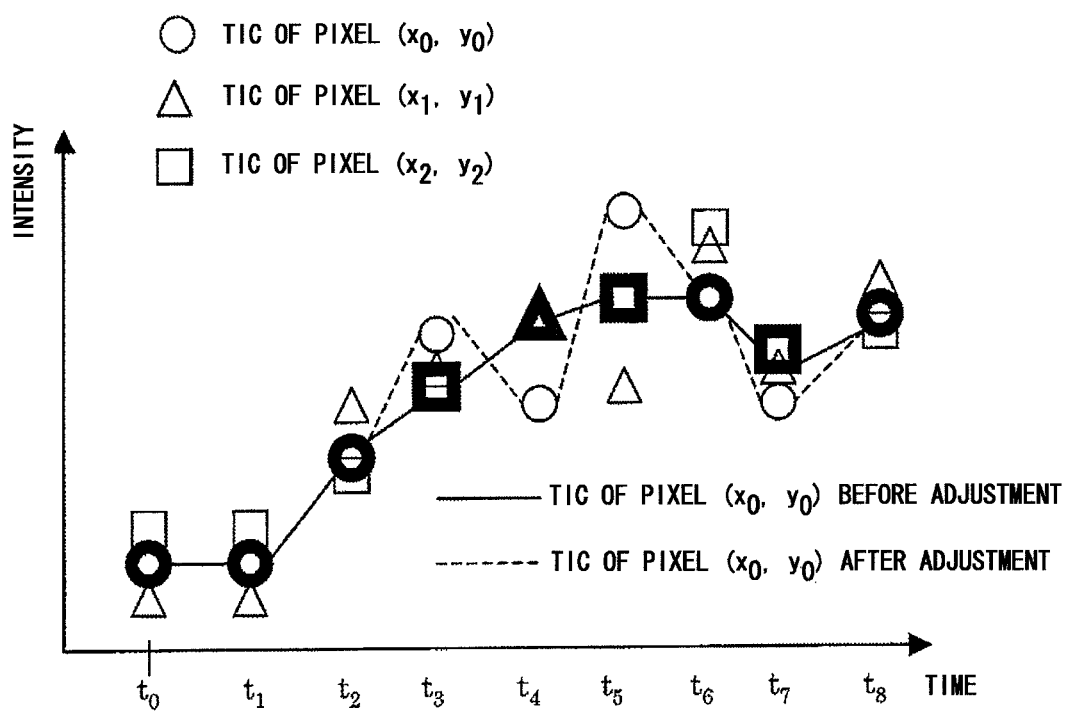
FIG. 8 illustrates a position adjustment method by smoothing the TIC according to the first embodiment.

There is another method for compensating for the influence of the displacement by selecting from a contiguous TIC, an intensity value to approach smoothing, on the premise that unevenness of the TIC is caused by the displacement. With reference to FIG. 8, processing details will be explained specifically as the following. FIG. 8 illustrates intensity changes of the pixel $(x_0, y_o)$, and two adjacent pixels $(x_1, y_1)$ and $(x_2, y_2)$, from the time $t_0$ to the time $t_8$, represented by circles, triangles, and squares, respectively. The TIC of the pixel $(x_0, y_0)$ before the compensation is significantly uneven from the time $t_3$ to the time $t_8$, as represented by the broken line in FIG. 8. The TIC of this pixel $(x_0, y_0)$ is subjected to the smoothing process as the following. Firstly, an average of the intensity values of the pixel $(x_0, y_0)$ at the time of $t_0$ and at the time of $t_2$ are obtained, and a value being the closest to this average value is selected from the intensity values of the respective pixels $(x_0, y_0)$, $(x_1, y_1)$ and $(x_2, y_2)$ at the time of $t_1$. The selected value is determined as the value of the pixel $(x_0, y_0)$ at the time $t_1$, and used for the TIC. Similarly, an average of the intensity values of the pixel at the time of $t_1$ and at the time of $t_3$ are obtained, and a value being the closest to this average value is selected from the intensity values of the respective pixels at the time of $t_2$. By repeating the processing above, unevenness of the focused pixel is adjusted and smoothed by using the intensity values of surrounding pixels, thereby generating the TIC as indicated by the solid line in FIG. 8. Here, it is assumed that the compensation process is performed by two contiguous pixels. However, the number of the pixels is not limited, and all the eight contiguous pixels may be used for the compensation, for instance. However, there is a relationship of tradeoffs between adjustment precision and processing load, and the pixel to be used for the adjustment is determined in seeking balance with the processing time.

Figure 9:
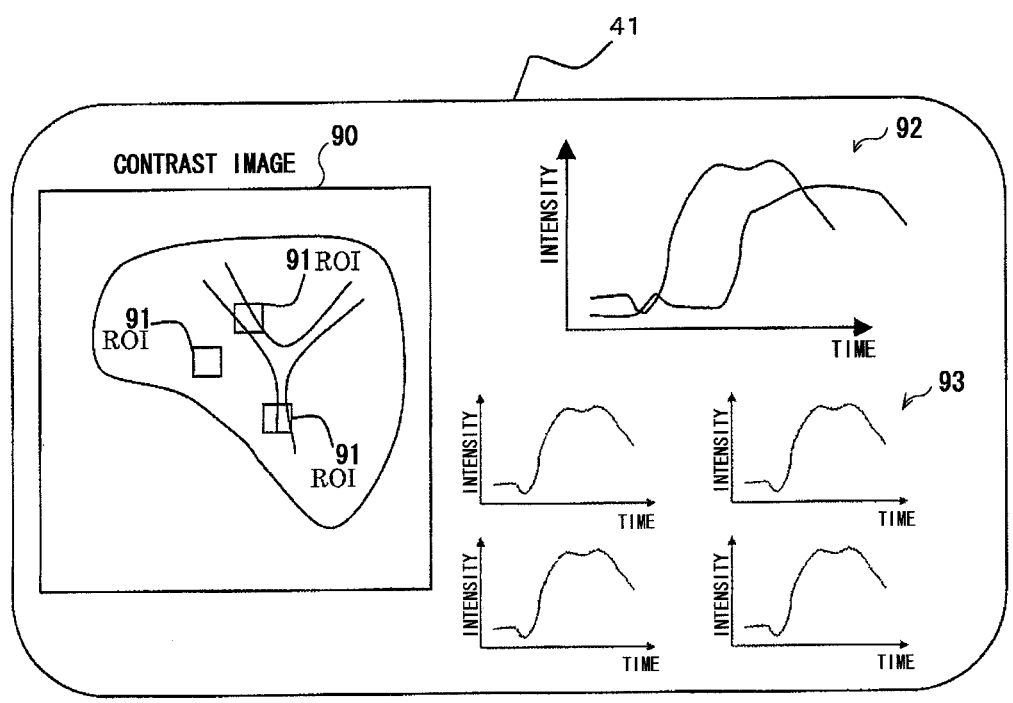
FIG. 9 illustrates an example of display mode (screen) according to the first embodiment.

In the step 103, the operator's manipulation of a predetermined switch on an operation panel or on a display screen triggers activation of the drawing information input unit 13, and a process is started for producing a color map representing blood flow dynamics. Simultaneously with starting the drawing information input unit 13, the image data items stored in the image memory 10 are reproduced in chronological order on the display unit 17, as a moving image (contrast image) 90 as shown in FIG. 9. The moving image on the display unit 17 may be an image held by the SC 9 after going through a compression processing, and directly passed to the display unit 17 to be displayed thereon.

As shown in FIG. 9, when the operator sets a region of interest 91 on the contrast image 90 being reproduced, the TIC of the region of interest and the contrast image 90 are displayed side by side on the display screen 41. More than one region of interest 91 may be set on arbitrary positions. If more than one TIC is displayed, the operator is allowed to freely select a display mode, a parallel display 93 or a superimposed display 92. Furthermore, the operator is allowed to freely edit the display mode, for example, the region of interest or the TIC designated by the operator is displayed in the superimposed display 92 and other TICs are displayed in the parallel display 93, or the like.

Figure 10:
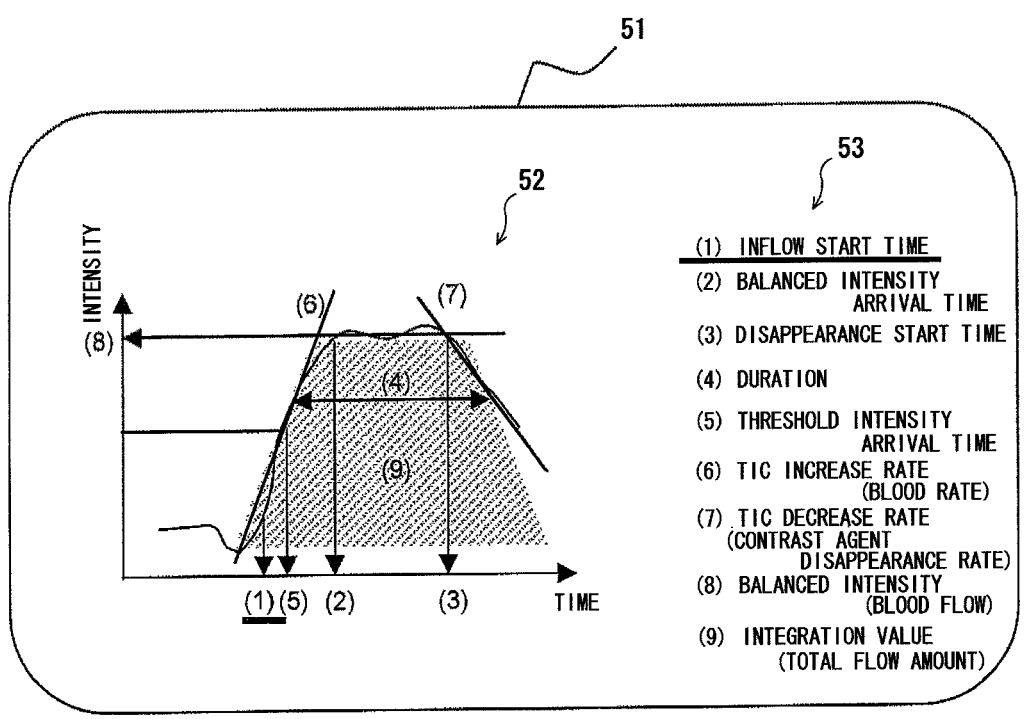
FIG. 10 illustrates an example of a navigation screen for selecting a drawing information item according to the first embodiment.

In the step 104, the operator selects from the drawing information list, a drawing information item as to which a color map is produced. The drawing information items are respectively associated with evaluation indexes (parameters) each representing a characteristic of the TIC. As shown in FIG. 10, the selection of the drawing information is performed on a navigation screen 51 displayed on the display unit 17. FIG. 10 illustrates one example of the navigation screen 51. The navigation screen 51 shows an appropriate TIC (a schematic view of the TIC or any of the TICs shown in FIG. 9) 52, and a typical drawing information list 53. Values or ranges associated with respective drawing information items are shown on the TIC 52.

Each of the drawing information items in the drawing information list 53 will be explained. "Inflow start time" represents the time when the contrast agent intravenously administered flows into a focused area and enhancement is started (indicated as numeral (1) on the TIC 52 in FIG. 10); "Balanced intensity arrival time" represents the time when the perfusion of the contrast agent is sufficient to reach the balanced state (indicated as numeral (2) on the same in FIG. 10); "Disappearance start time" represents the time when the contrast agent starts disappearing after the balanced state, and the TIC begins declining (indicated as numeral (3) on the same in FIG. 10); "Duration" represents the time from the point when the intensity reaches a threshold until the intensity again reaches the threshold due to the disappearance of the contrast agent (indicated as numeral (4) on the same in FIG. 10); "Threshold intensity arrival time" represents the time when the intensity reaches the threshold (indicated as numeral (5) on the same in FIG. 10); "TIC increase rate" represents an index reflecting a blood speed, being a rate of TIC change per time unit from starting enhancement until reaching the balanced state (indicated as numeral (6) on the same in FIG. 10); "TIC decrease rate" represents an index reflecting a rate of contrast agent disappearance, being a rate of TIC change per time unit when the TIC drops from the balanced state (indicated as numeral (7) on the same in FIG. 10); "Balanced intensity" represents an index reflecting a blood flow, being an intensity value when the contrast agent perfusion is sufficient to reach the balanced state (indicated as numeral (8) on the same in FIG. 10); and "Integration value" represents an index indicating a total flow amount during the time for acquiring the TIC, being a time integration value (indicated as the diagonally shaded area with numeral (9) in FIG. 10).

The operator manipulates a pointer displayed on the display unit 17 and chooses a desired number, thereby selecting a drawing information item from the drawing information list 53. As shown in FIG. 10, the drawing information item being selected and associating number on the TIC 52 are highlighted using an underline, boldface, or the like, thereby facilitating an identification of the item being selected.

The order of the drawing information items in the drawing information list 53 displayed on the navigation screen 51 may be configured as the following, for example; ranking the items according to a frequency how often the operator selected the item in the past, according to a level of significance for tumor diagnosis, or the like, and the drawing information items are displayed in such a manner that the higher ranked item is listed on the upper portion. It is further possible to configure such that the operator is allowed to freely change the sequence of the drawing information items.

It is configured such that a threshold required for calculating the threshold intensity arrival time and the duration is set according to the operator who moves the arrows provided on the TIC 52 in FIG. 10 (arrows indicated by (5) and (4) in FIG. 10). On this occasion, there is additional configuration that the intensity value associated with the position designated by the arrow is also displayed on the navigation screen 51.

It is to be noted that the drawing information items in the drawing information list 53 in FIG. 10 are just examples, and it is configured such that the operator is allowed to freely edit the drawing information; adding or deleing items, changing the displayed text, defining a new drawing information item that can be acquired based on the TIC, and the like.

Figure 11:
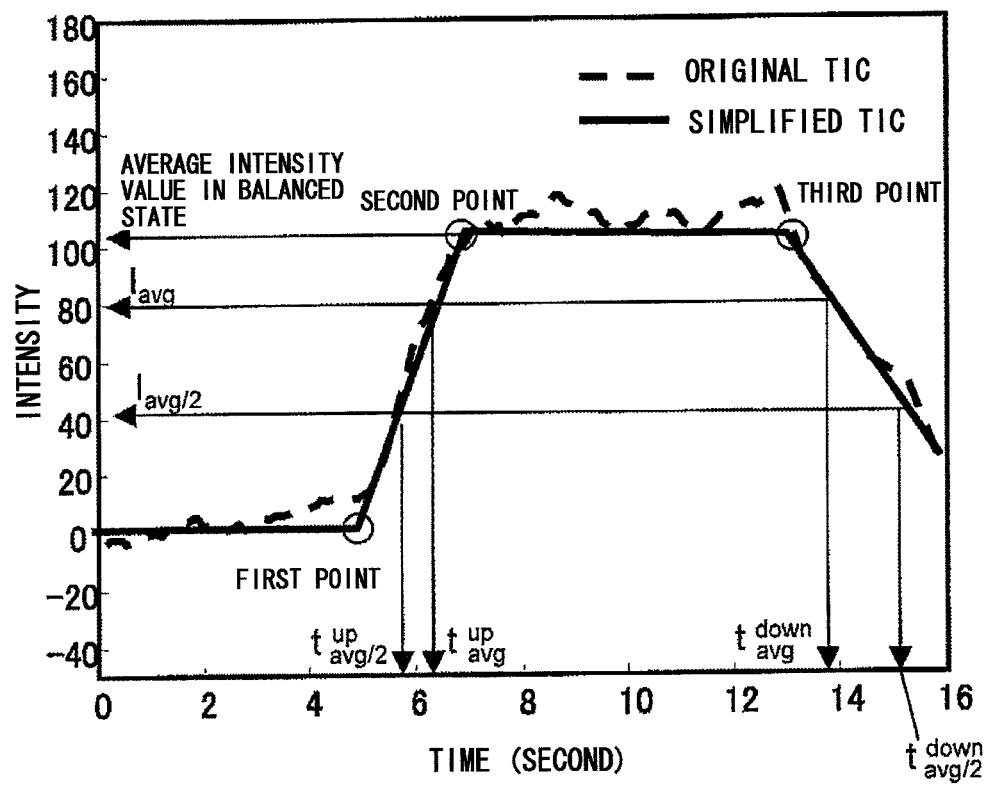
FIG. 11 illustrates a simplification process of the TIC according to the first embodiment.

In the step 105, the parameter calculation unit 14 calculates a value of the parameter (evaluation index) associated with the drawing information item that is selected in the step 104. Firstly, the TIC generated by the TIC operation part 12 is simplified to be a form of function which has a typical TIC characteristic being predetermined, and a value of the parameter is calculated as to this simplified TIC. FIG. 11 illustrates the TIC (broken line) generated by the TIC operation part 12, and the TIC (straight line) that is simplified by the predetermined function. The predetermined function takes the form that starts from the time when the intensity value is zero, linearly increases from the first point, reaches the intensity value in the balanced state at the second point, and after a certain period of balanced state, linearly drops from the third point. Hereinafter, a method for generating the TIC simplified by the predetermined function, and parameters obtained as to the TIC being simplified will be explained. Firstly, a gradient is calculated, indicating the increase of the intensity from the first point to the second point. Time lengths taken until reaching an average intensity value ($I_{ave}$) and ½ of the average intensity value ($I_{ave}/2$) (expression 1 and expression 2) are obtained from the TIC being time-averaged, for each of increasing time and decreasing time. Then, by using these values, an intensity change per unit time is obtained according to the expression 3 and expression 4, and these are assumed as parameter values respectively associated with "TIC increase rate" and "TIC decrease rate" of the drawing information.

$$t_{avg}^{up}, t_{avg/2}^{up}$$ [Expression 1]

$$t_{avg}^{down}, t_{avg/2}^{down}$$ [Expression 2]

$$\frac{(I_{avg} - I_{avg/2})}{(t_{avg}^{up} - t_{avg/2}^{up})}$$ [Expression 3]

$$\frac{(I_{avg} - I_{avg/2})}{(t_{avg}^{down} - t_{avg/2}^{down})}$$ [Expression 4]

A straight line is extended, connecting two measurement points (expression 5, expression 6) which are determined from the values used in calculating the increase rate, and a time point when the straight line reaches the intensity value zero is assumed as the first point. The time at the first point corresponds to a parameter value being associated with the "Inflow start time" of the drawing information.

$$(t_{avg}^{up}, I_{avg})$$ [Expression 5]

$$(t_{avg/2}^{up}, I_{avg/2})$$ [Expression 6]

Next, the average intensity value of the TIC is recalculated in the range as indicated by the expression 7. This value is assumed as a parameter value being associated with the "Balanced intensity" of the drawing information.

$$[t_{avg}^{up}, t_{avg}^{down}]$$ [Expression 7]

In the same manner as the case where the first point is calculated, a time point is obtained when an extended straight line connecting two measurement points (expression 5, expression 6) used in calculating the "TIC increase rate" reaches the balanced intensity value, and this obtained time point is assumed as the second point. This value is assumed as a parameter value being associated with the "Balanced intensity arrival time". Similarly, a time point is obtained when an extended straight line connecting two measurement points (expression 8, expression 9) used in calculating the "TIC decrease rate" reaches the balanced intensity value, and this obtained time point is assumed as the third point. This value is assumed as a parameter value being associated with the "Disappearance start time".

$$(t_{avg}^{down}, I_{avg})$$ [Expression 8]

$$(t_{avg/2}^{down}, I_{avg/2})$$ [Expression 9]

If the drop of the TIC does not reach $I_{avg}/2$, the time at the third point is assumed as the end time of the measurement (data acquisition), and the intensity at the third point is assumed as a balanced intensity value, on the presumption that the balanced state continues from the second point.

As for the "Duration", "Threshold intensity arrival time", and "Integration value", the operator is allowed to directly input the threshold and those items can be calculated from the TIC without any particular processing as described above. Therefore, the simplification process is not necessarily required. However, by calculating a value indicating the characteristic of the TIC in advance, it is possible to immediately reflect any change in the drawing information on the color map.

In order to reduce the load on the image memory 10, it is further possible to restrict the information stored for each pixel constituting the image data to; the initial value of the TIC, the first point, the second point, the third point, and the TIC decrease rate, which are calculated in the TIC simplification process. With those five information items, an overview of the TIC of each pixel can be reproduced, thereby enabling the color map to be produced.

As for the predetermined function, the function $y = A(1-e^{-\beta t})$ is defined, assuming that the balanced intensity is A, the time is t, and the intensity change along with the inflow of the contrast agent is β, starting from the first point, and the values A and β, which characterize the TIC, may be held according to a generally known fitting process. In addition, the time for starting the contrast agent inflow may be introduced as a parameter $t_0$, and the function is defined as; $y=A(1-e^{-\beta(t+t0)})$ and it is also defined here; y=A, if $0<t<t_0$. Accordingly, it is possible to subject the data from a stage before the contrast agent inflow, to the fitting process.

In the step 106, based on the values of the parameters calculated in the step 105, a color map is produced being color-coded pixel by pixel, according to magnitude of each value.

Figure 12:
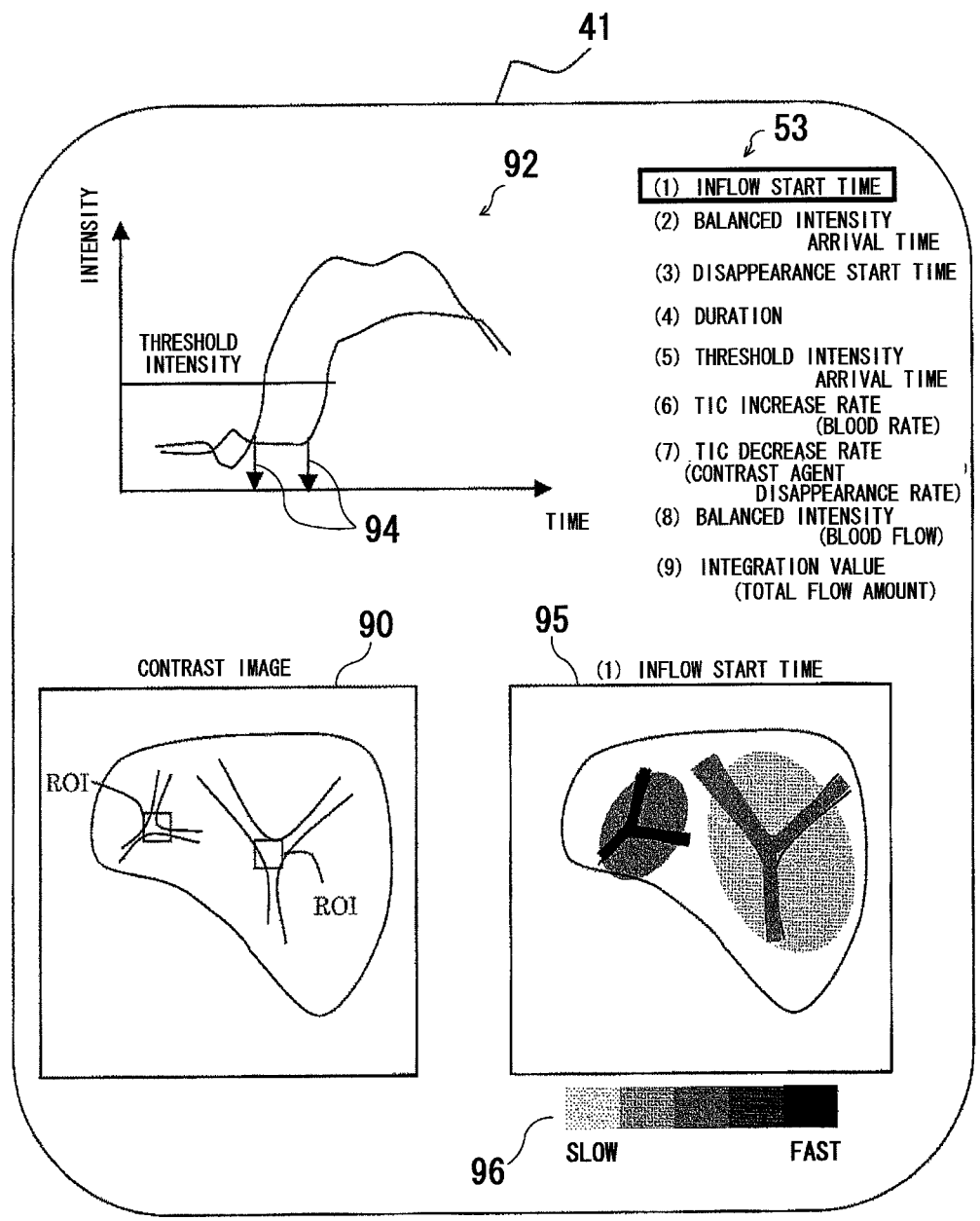
FIG. 12 illustrates an example of display mode (screen) of the color map according to the first embodiment.

FIG. 12 illustrates an example of display mode of the color map. On the display screen 41 of the display unit 17, there are displayed a contrast image 90 being the stored image data, a superimposed display 92 of the TICs associated with the selected region of interest, arrows 94 indicating the selected drawing information and associated values on the superimposed display 92, and a color map 95 representing values associated with the drawing information, color-coded pixel by pixel. The color map 95 is accompanied with a color bar 96 representing association of parameter values with colors. The association of parameter values with colors is configured to be freely modified by the operator. For example, it is allowed to change association of color gradation, shading, or the like, with magnitude of the parameter values. The color bar 96 may also be configured to represent quantitative information, by displaying actually calculated parameter values, in addition to qualitative information such as "slow" and "fast".

Figure 13:
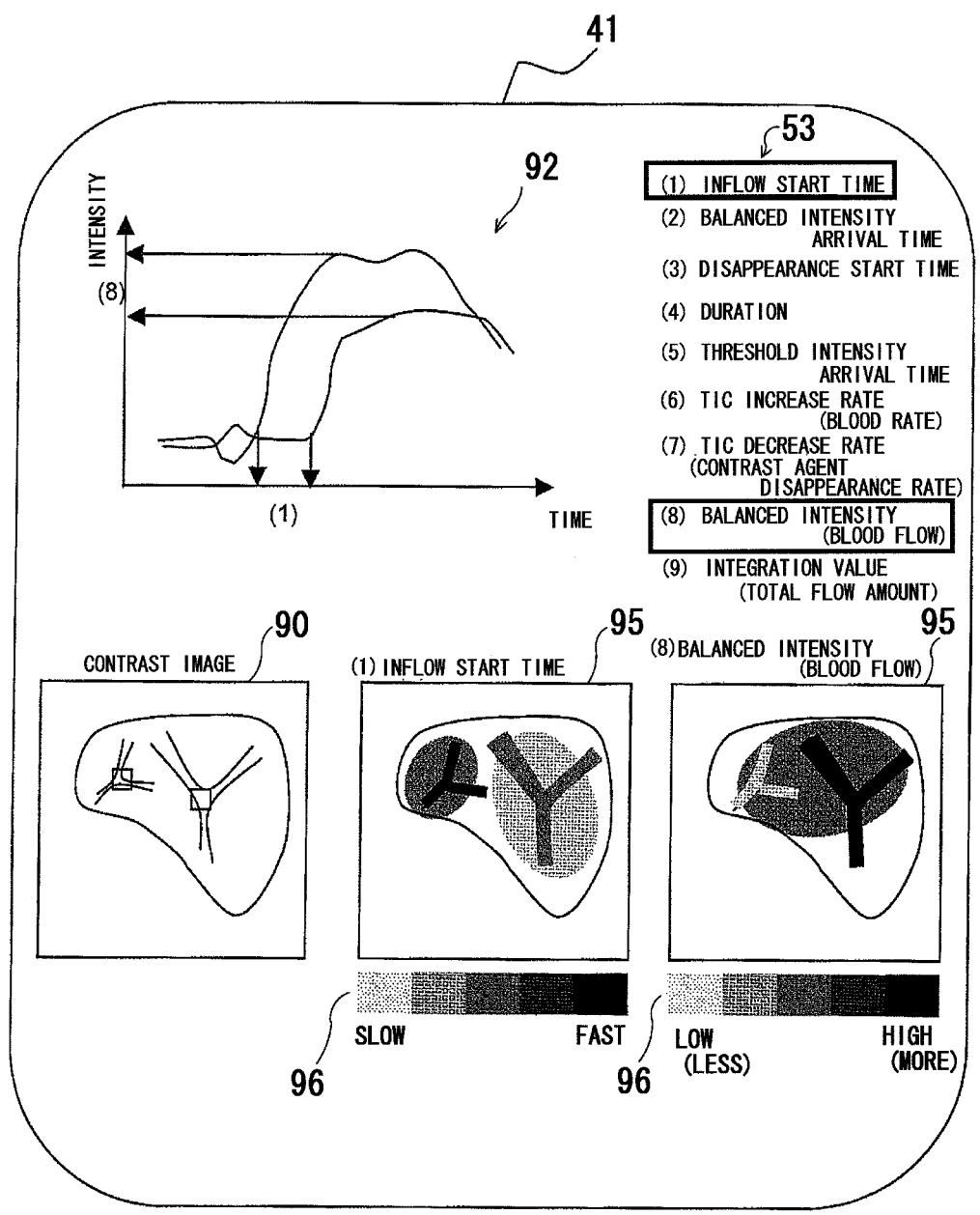
FIG. 13 illustrates an example of display mode (screen) in the case where the color maps are displayed side by side according to the first embodiment.

The operator is allowed to freely change the selection of drawing information. If the operator selects more than one drawing information item, as shown in FIG. 13, it is configured in such a manner that multiple color maps 95, respectively associated with the selected drawing information items, are displayed side by side on the display screen 41 of the display unit 17. Since multiple color maps 95 are displayed side by side, it is possible to easily compare a difference in blood flow and the inflow start time.

In the case of liver tumor, a vessel as a starting point of the tumor vessel, a blood flow in the tumor tissue, and the like, serve as significant information for diagnosis. Since the color maps, respectively representing the "Inflow start time", "Balanced intensity", "Integration value", or the like, are displayed side by side for comparison, it is possible to evaluate a distribution, density, or the like, of the vessels and tumor tissues which are proliferating from arteries, for instance.

It is configured such that the operator is allowed to freely combine and select as information to be displayed, one or at least two of the following; the TIC superimposed display 92, the drawing information list 53, the contrast image 90, and the color map 95, and the operator is also allowed to freely edit the arrangement and the size thereof.

Next, an explanation will be made as to the display mode of the color map 95.

The display mode of the color map 95 may be modified on the basis of either the color bar 96 or the color map 95.

Figure 14:
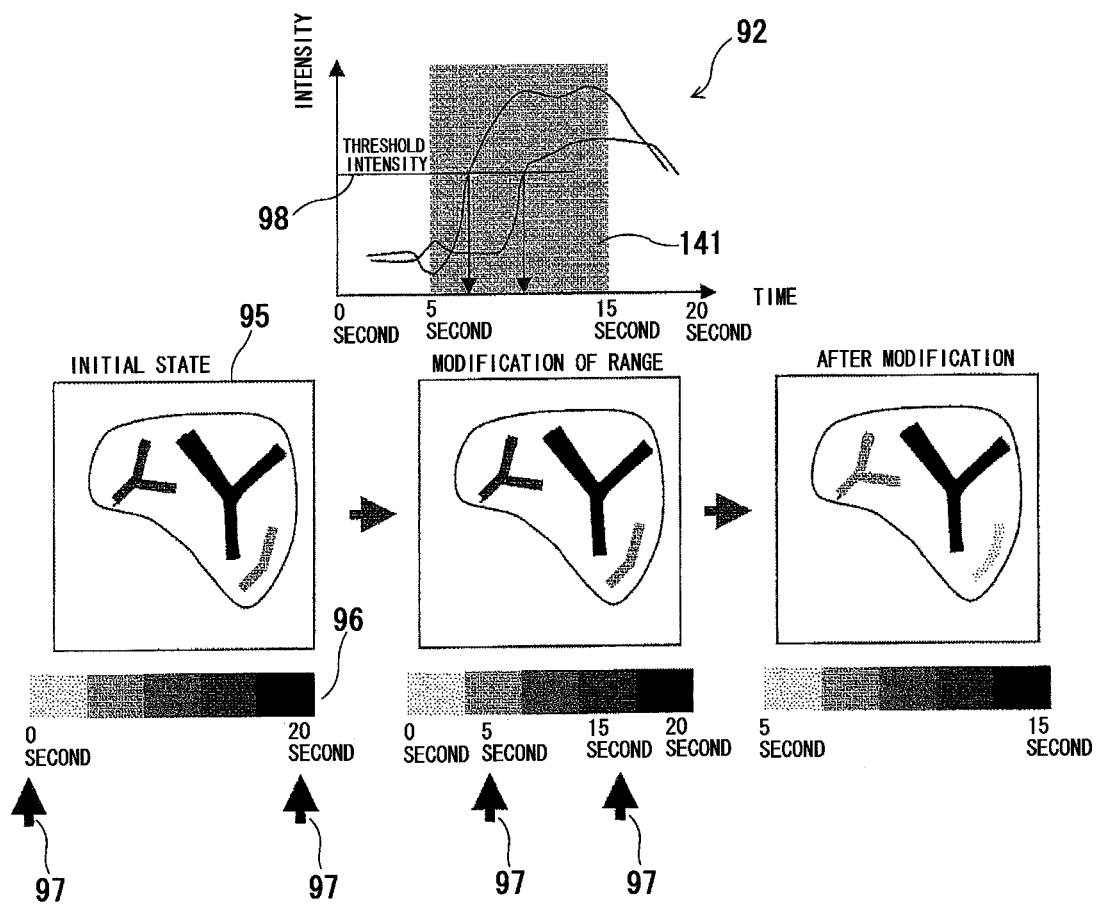
FIG. 14 illustrates a modification of color range according to the first embodiment.

When the display mode of the color map 95 is modified on the basis of the color bar 96, the procedure is as the following. In the step 107, as shown in FIG. 14, two arrows 97 are displayed on the color bar 96. The operator manipulates the arrows 97 to move on the display screen 41, thereby restricting an area of the color focused on the color map, i.e., a range of parameter values, so as to optimize the color within the area. For example, as for the color bar 96 of the color map 95 representing the "Threshold intensity arrival time", when the display is restricted to the range from 5 seconds to 15 seconds, the redistribution of color is performed within the range being restricted from 5 seconds to 15 seconds. Simultaneously, as shown in FIG. 14, the area indicating the restricted range (5 seconds to 15 seconds) is displayed on the TIC superimposed display 92. This process for restricting the range of the parameter value may be performed using the values on the TIC as a reference. For example, it may be configured such that the operator may modify the range by designating the time and the intensity range for evaluation on the TIC superimposed display 92. Narrowing appropriately the range of the parameter value may allow a display of the area showing similar blood flow dynamics with an emphasis thereon.

Modification of the display mode on the basis of the color map 95 is performed as the following. In the area where there is no contrast agent perfusion, accurate parameters are not calculated, and in some cases, the area may be displayed as a noise on the color map. In order to eliminate the area having no contrast agent perfusion from the color map, as shown in FIG. 14, it is configured such that threshold intensity 98 is set on the TIC superimposed display 92, and the area that does not go over the threshold is set to be zero on the color map 95. In addition, a median filter is applied appropriately if required, thereby removing mosaic generated on the color map 95, and visibility is improved.

Figure 15:
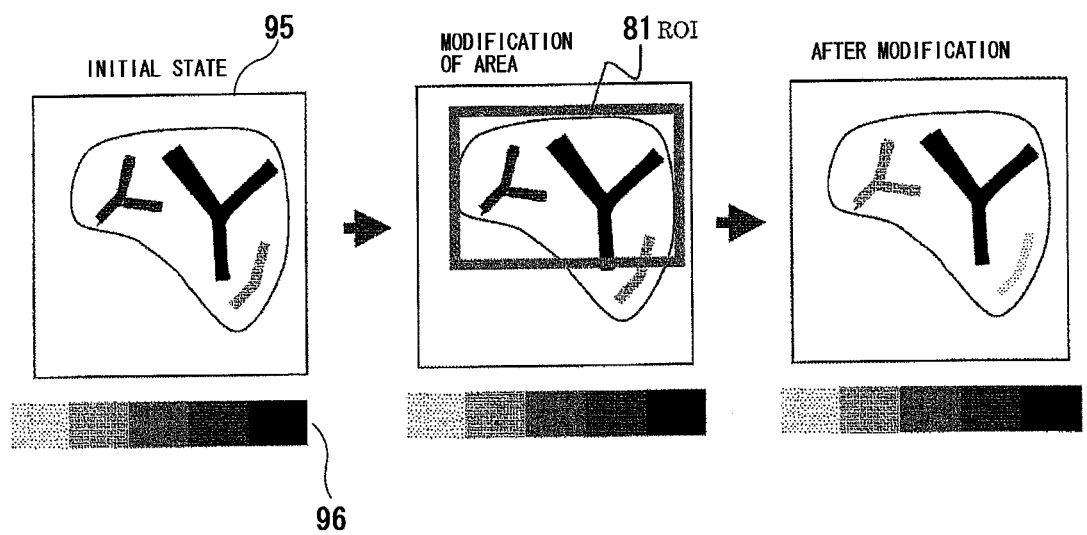
FIG. 15 illustrates a modification of color range by redistributing colors within a region of interest on the color map according to the first embodiment.

As shown in FIG. 15, a region of interest 81 can be set on the color map 95, and it is further possible to configure such that the color may be redistributed in the range of the region of interest 81. With this processing, the color range of the focused area can be expanded, and thereby allowing a clear distinction of minor differences in parameter values, according to the color variation.

Figure 16:
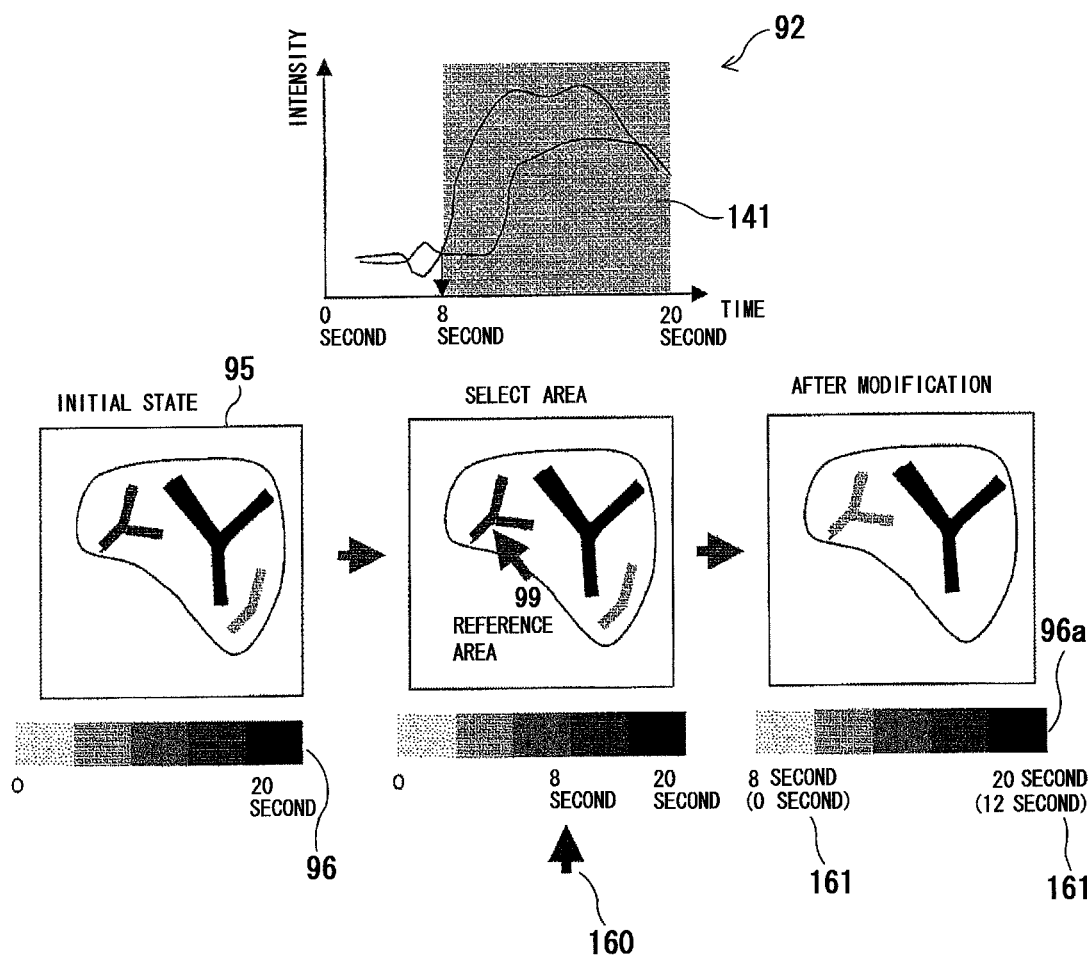
FIG. 16 illustrates a modification of color range by redistributing colors with respect to a reference area on the color map according to the first embodiment.

As shown in FIG. 16, it is further possible to configure such that when the reference area 99 is set on the color map 95, the color may be redistributed using the parameter values of the reference area 99 as a standard. For example, in the case of the color map representing the "Inflow start time", when the operator designates a particular vessel as the reference area 99, a position of the color being associated with the vessel is displayed on the color bar 96 using the arrow 160. Here, the range of the color bar is displayed from 0 second to 20 seconds, and the arrow 160 is displayed at the position of 8 seconds, being the parameter value of the reference area 99. Upon fixing the reference area 99, the color is redistributed using the parameter values starting from 8 seconds, and the color map 95 is reconstructed. The color bar 96 is reconfigured indicating the reference range from 8 seconds to 20 seconds. On the color bar 96, converted values 161 assuming the parameter value of the reference area 99 as zero, are put along with the original parameter values (for example, on the color bar 96a of FIG. 16, the converted values 161 are included in parentheses). The restricted parameter range is displayed on the TIC superimposed display 92 as shown in FIG. 16. It is further possible to configure such that the operator modifies the range on the TIC superimposed display 92, thereby adjusting the range of the parameter. According to this processing, timing difference may be evaluated in detail, regarding the start of contrast agent inflow, as to the vessel that is assumed as the reference.

Figure 17:
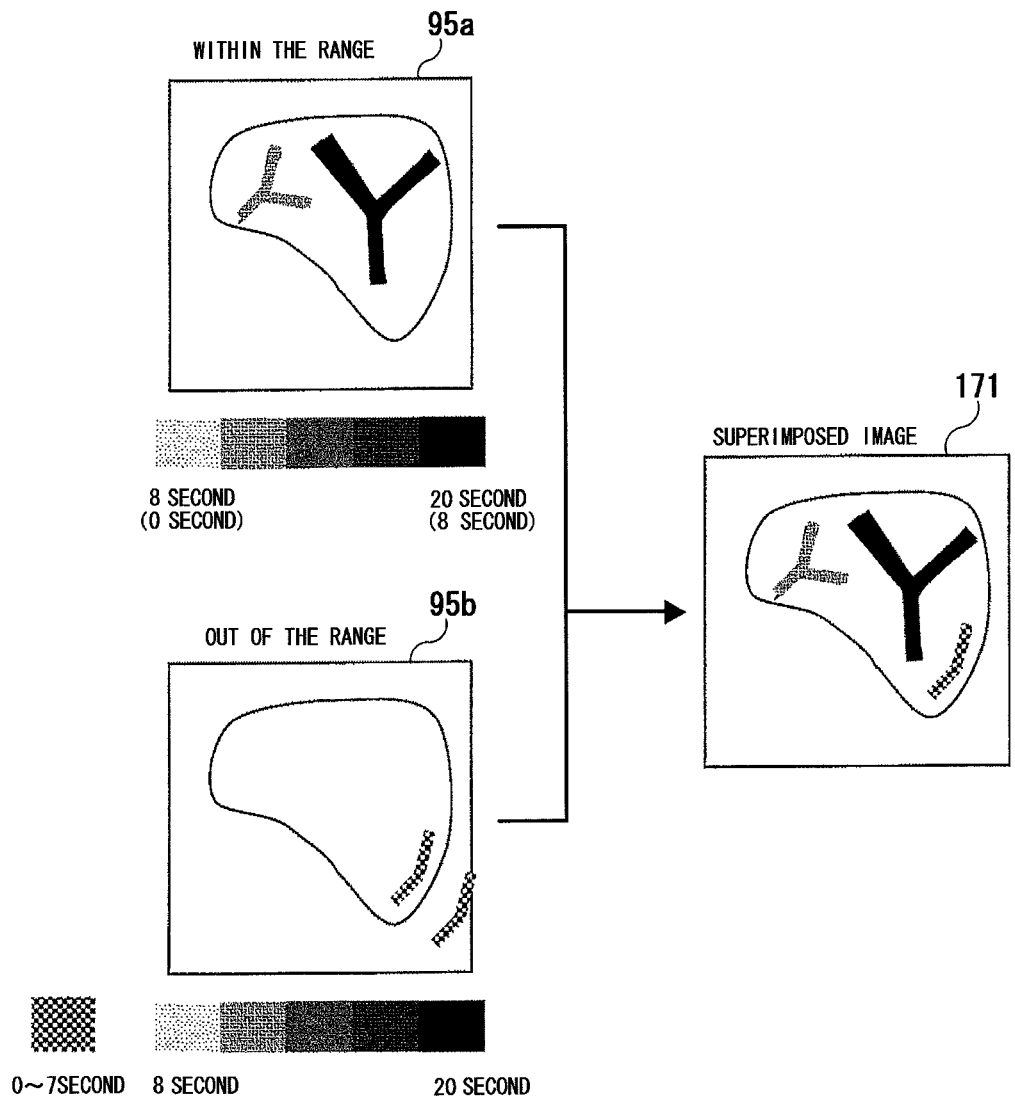
FIG. 17 illustrates an image obtained by superimposing the information that falls outside the color range according to the first embodiment.

Due to the modification of the color map area or the parameter range, an area which is off the range defined by the color bar disappears from the color map. Therefore, there is a possibility that it becomes difficult to obtain an overall image. In order to compensate for missing information, it is possible to configure such that a color for displaying the missing information is set on the color bar, and the color is superimposed on the color map for the compensation. For example, as shown in FIG. 16, in the case of the color map representing the inflow start time, the parameters are restricted to the range from 8 seconds, the information from zero to 7 seconds is missing. Given this situation, as shown in FIG. 17, an image of a color map 95b from zero to 7 seconds, being off the range, is prepared together with the image of the color map 95a within the range constituted by the parameter values from 8 seconds to 20 seconds, and it is possible to produce a superimposed image 171 on which both images are superimposed one on another.

The aforementioned modification of the display mode of the color map is carried out on the basis of the color bar or the color map, and each of such modifications is also reflected on the TIC superimposed display 92. Therefore, it is also possible to modify the display mode based on the TIC superimposed display 92. As shown in FIG. 14 and FIG. 16, another configuration is conceivable as the following; the operator sets an area 141 restricting the parameter range on the TIC, and this setting is reflected on the color map 95 and on the color bar 96.

Figure 18:
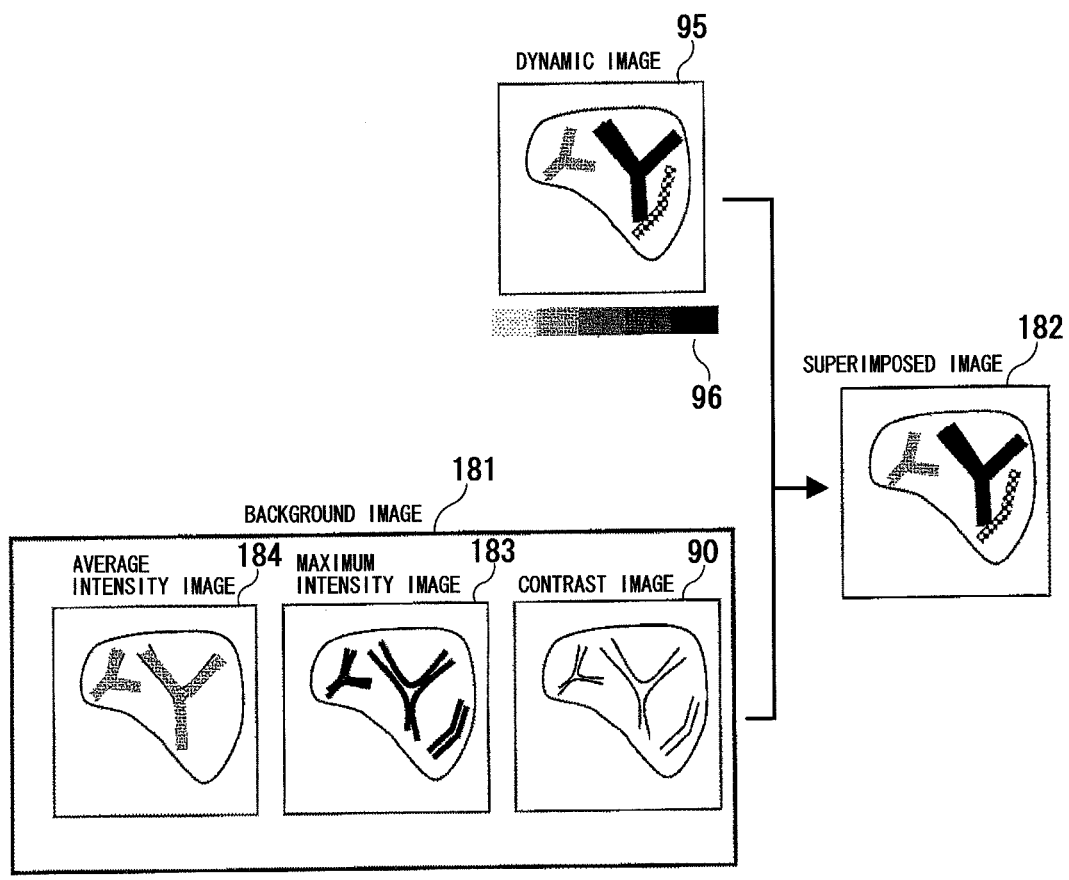
FIG. 18 illustrates an image obtained by superimposing the color map on a background image according to the first embodiment.

As shown in FIG. 18, it is further possible that a specific contrast image 90 is selected from the reproduced images, and this contrast image 90 is set as a background image 181 on which the color map 95 is superimposed, thereby generating and displaying a superimposed image 182. The background image 181 may be an image which is obtained by subjecting a stored image to an imaging process such as vessel enhancement. As one example, an maximum intensity image 183 or an average intensity image 184 may be employed, which are obtained according to a process for enhancing the vessel structure, by calculating the maximum intensity or the average intensity from the TIC generated as to each pixel. It is further possible to display multiple color maps 95, in such a manner as superimposing one on another. Here, the background image 181 is not limited to the contrast image, but other images may be applicable, such as an image representing tissue elasticity, a CT image, an MR image, and a PET image.

With the configuration above, in addition to the color map, various medical images, such as a generally known ultrasonic image including Doppler and contrast image, a CT image, and an MR image, are allowed to be displayed side by side or in a manner as superimposing one on another. Therefore, it is possible to display images specific to the information that is required by the operator.

Displaying multiple color maps side by side may facilitate comparison of primary tumor vessels, blood flow of the tumor tissue, and expanding direction of enhancement of the tumor tissue, which are significant for differential diagnosis of the liver tumor. In addition, comparison of the color maps before and after treatment is conceivable to be effective for determination of efficacy of the treatment. There is a treatment method that blocks the tumor vessel by using a laser, a drug, a high-sound pressure ultrasonic wave, or the like, so as to necrotize downstream tissue. In order to carry out this method, the configuration of the present embodiment, such as displaying color maps side by side, is effective in the entire process of the treatment, including a decision of the vessel as a target for the blockage, checking the blocked state, checking the treatment result, and judgment of the treatment effect.

Information inputted into the TIC arithmetic and control unit 11, the drawing information input unit 13, and the display information input unit 15 may be configured as inputted by the operator in advance. Alternatively, it may be configured as automatically set initially, eliminating input works by the operator. On this occasion, the descriptions of the initial settings are packaged depending on medical application, thereby simplifying the initial setting process. For example, in a usage for diagnosing liver tumor, it is significant to know an aspect of the tumor vessel and the tumor tissue. In other words, followings serve as significant indexes; timing of enhancement start of the tumor vessel and the tumor tissue when the heart is set as a starting point, an amount of the contrast agent which the Kupffer cells in the liver take in, and the like. Therefore, minimum required information items such as the "Inflow start time", "Duration", and "Integration value" are packaged in advance, being selected from the drawing information list 53 as shown in FIG. 10, and the package is configured to be selectable as drawing information for tumor diagnosis. With this configuration, the operator is allowed to eliminate a work for inputting detailed settings and display necessary information automatically, by selecting an item (package) of the drawing information for tumor diagnosis.

Second Embodiment

Hereinafter, with reference to the accompanying drawings, the second embodiment of the present invention will be explained.

Figure 19:
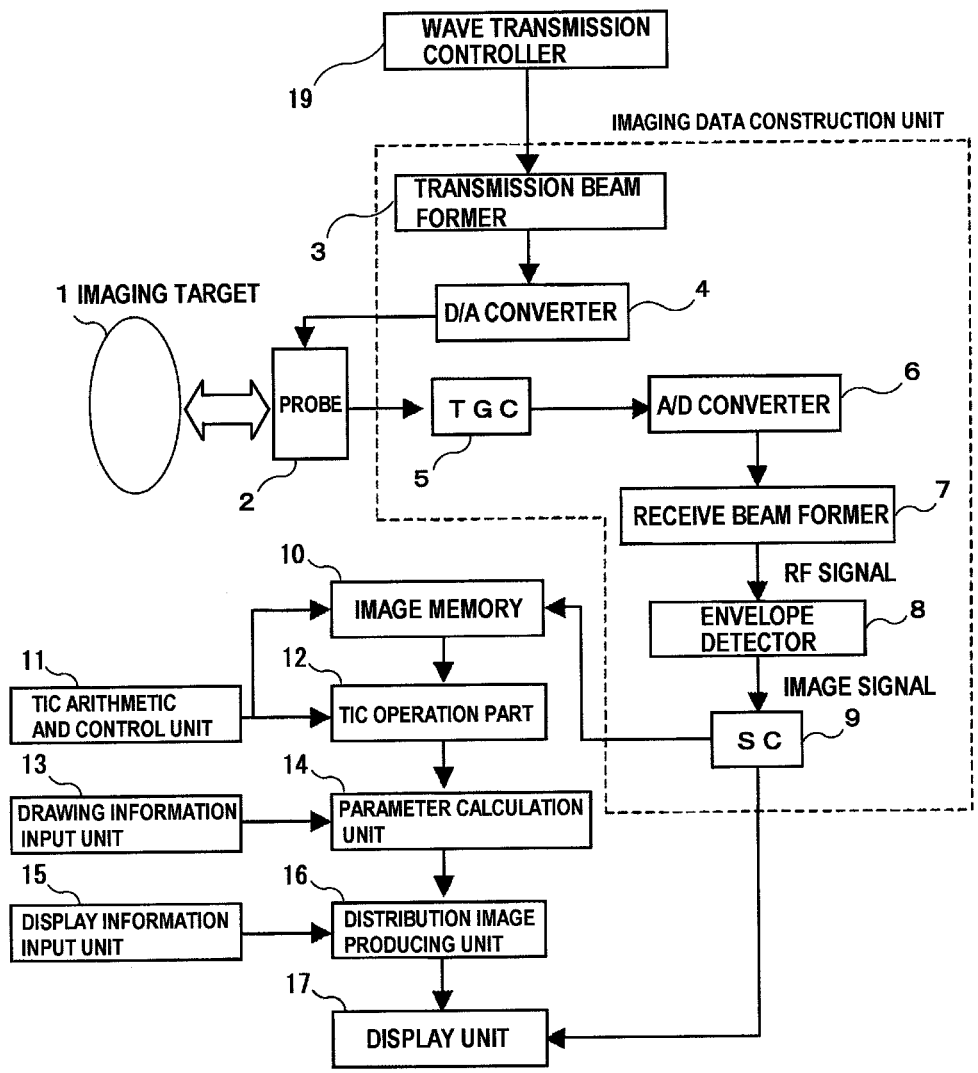
FIG. 19 is a block diagram showing a configuration example of the ultrasonic diagnostic apparatus according to a second embodiment.

The ultrasonic diagnostic apparatus (image display apparatus) according to the second embodiment relates to a technique which three-dimensionally expands the technique described as the first embodiment. FIG. 19 illustrates a configuration of the apparatus. A shape, an internal structure, and an operation mode of the probe 2 are not particularly limited, as far as it is capable of imaging three-dimensional information. It may be a probe having a one-dimensional array as described in the first embodiment, mechanically movable with a drive unit such as a motor, or a probe having a two-dimensional array.

The transmission beam former 3 is provided with a wave transmission controller 19, which controls a wave transmission sequence for acquiring image data of multiple different cross sections. The wave transmission sequence is determined according to a size of the area (orientation direction, depth direction, and slice direction) for acquiring three-dimensional information, a frame rate of the image data, and sampling interval of the image data upon generating a TIC. The sampling interval of the image data for generating the TIC is required to be around 4 Hz as described in the first embodiment. Therefore, when the frame rate of the image data is 20 Hz, it is possible to take images of five cross sections at the maximum, on different positions in the slice direction. When the width of the area in the slice direction for acquiring three-dimensional information is set to be 5 mm, the distance between imaging planes is 1 mm, and this value is set as a distance which the probe shifts in the slice direction upon imaging. In order to increase the number of the imaging planes and the sampling intervals of the TIC, it is recommended to increase the frame rate for acquiring the image data. For that purpose, adjustments are made depending on the usage of the operator, such as narrowing the width of the area in the orientation direction or in the depth direction, in such a manner as including the focused area.

Since generation of TIC from the acquired image data, inputting of drawing information, calculation of parameter values, and various display modes displayed on the display unit 17 are the same as those in the first embodiment, tedious explanation will not be made. Next, processing in the distribution image producing unit 16 will be explained.

Figure 20:
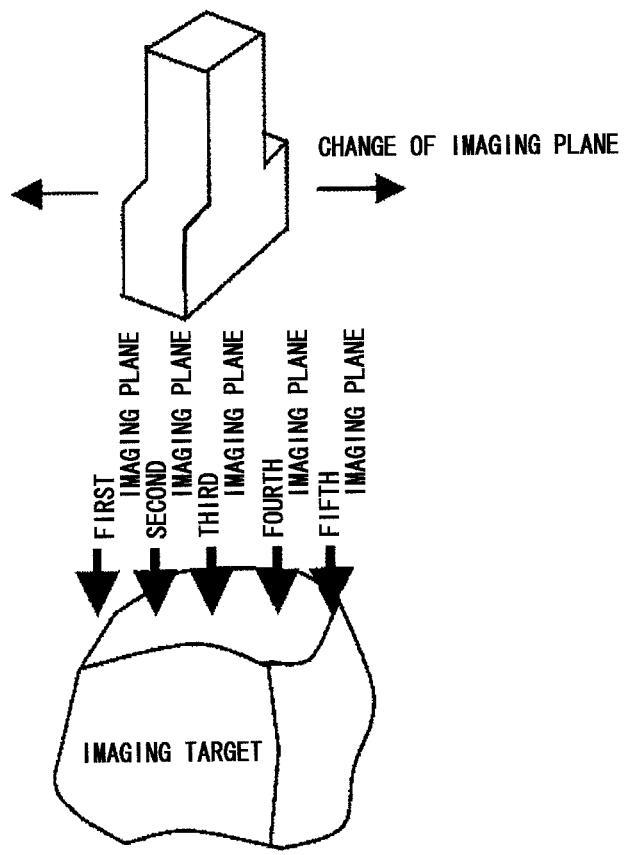
FIG. 20 illustrates a positional relationship of different imaging planes according to the second embodiment.
Figure 21:
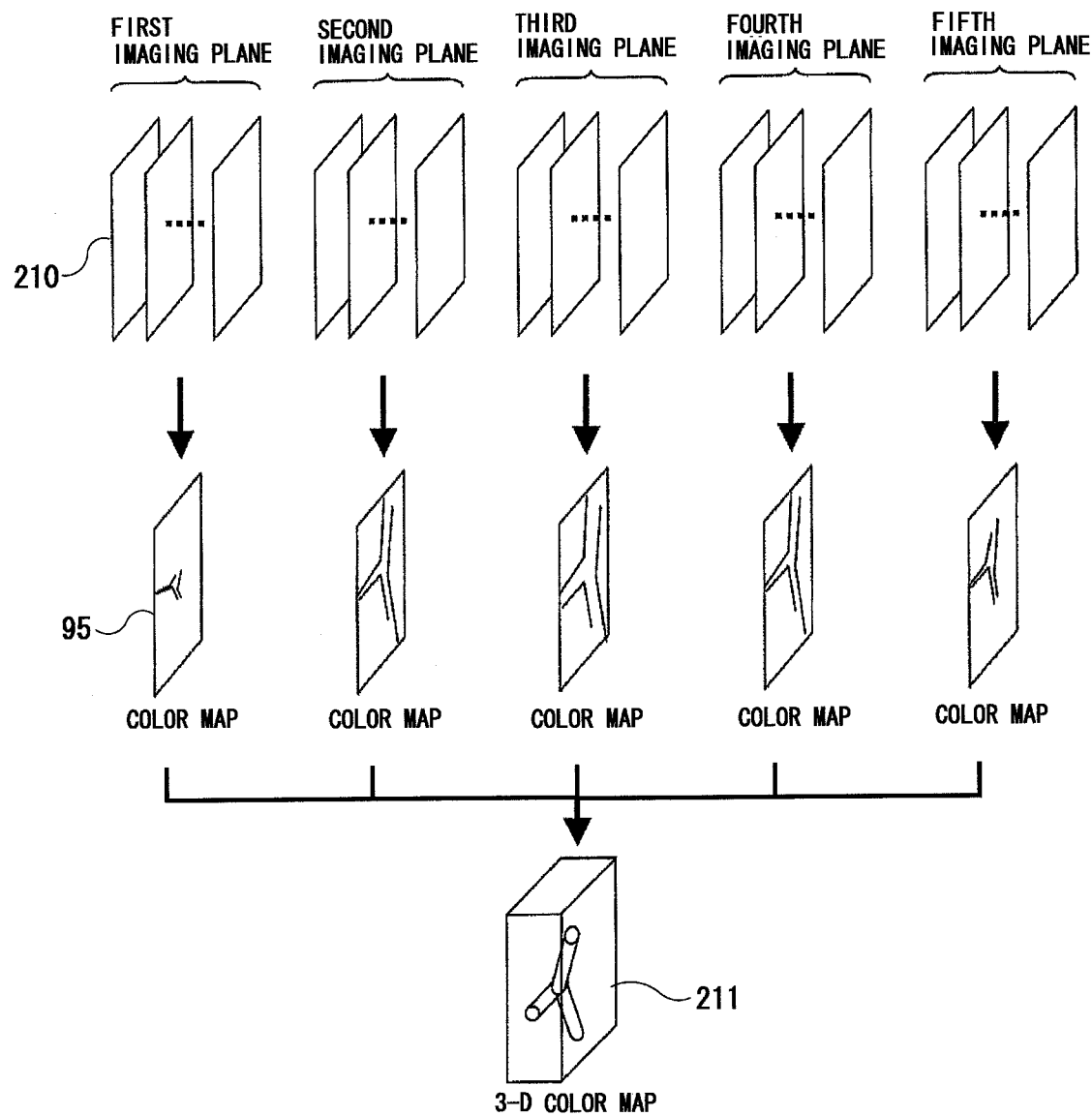
FIG. 21 illustrates a configuration of 3-D color map made up of image data on each of the imaging planes according to the second embodiment.

By way of example, as shown in FIG. 20, it is assumed that the probe having one-dimensional array is moved in the slice direction to take images at five different positions from the first imaging plane to the fifth imaging plane. Imaging sequentially from the first imaging plane to the fifth imaging plane is taken in the wave transmission sequence, and this is assumed as one scan which is repeated until the operator terminates measurement. As shown in FIG. 21, the acquired image data items 210 are sorted by each imaging plane, and TIC generation and calculation of parameter values are performed with respect to each imaging plane. Thereafter, the two-dimensional color maps 95 are produced for each imaging plane. A noise removing filter, such as a median filter, is applied to each of the color maps 95. Each of the color maps 95 two-dimensionally produced is arranged three-dimensionally at a distance of between each of the imaging planes targeted for imaging. Space between the imaging planes is subjected to pixel interpolation according to a linear interpolation process or the like, thereby producing a 3-D color map 211. With this three-dimensionally produced color map, it is possible to observe three-dimensionally a difference in the blood flow dynamics in the tissues.

Figure 22:
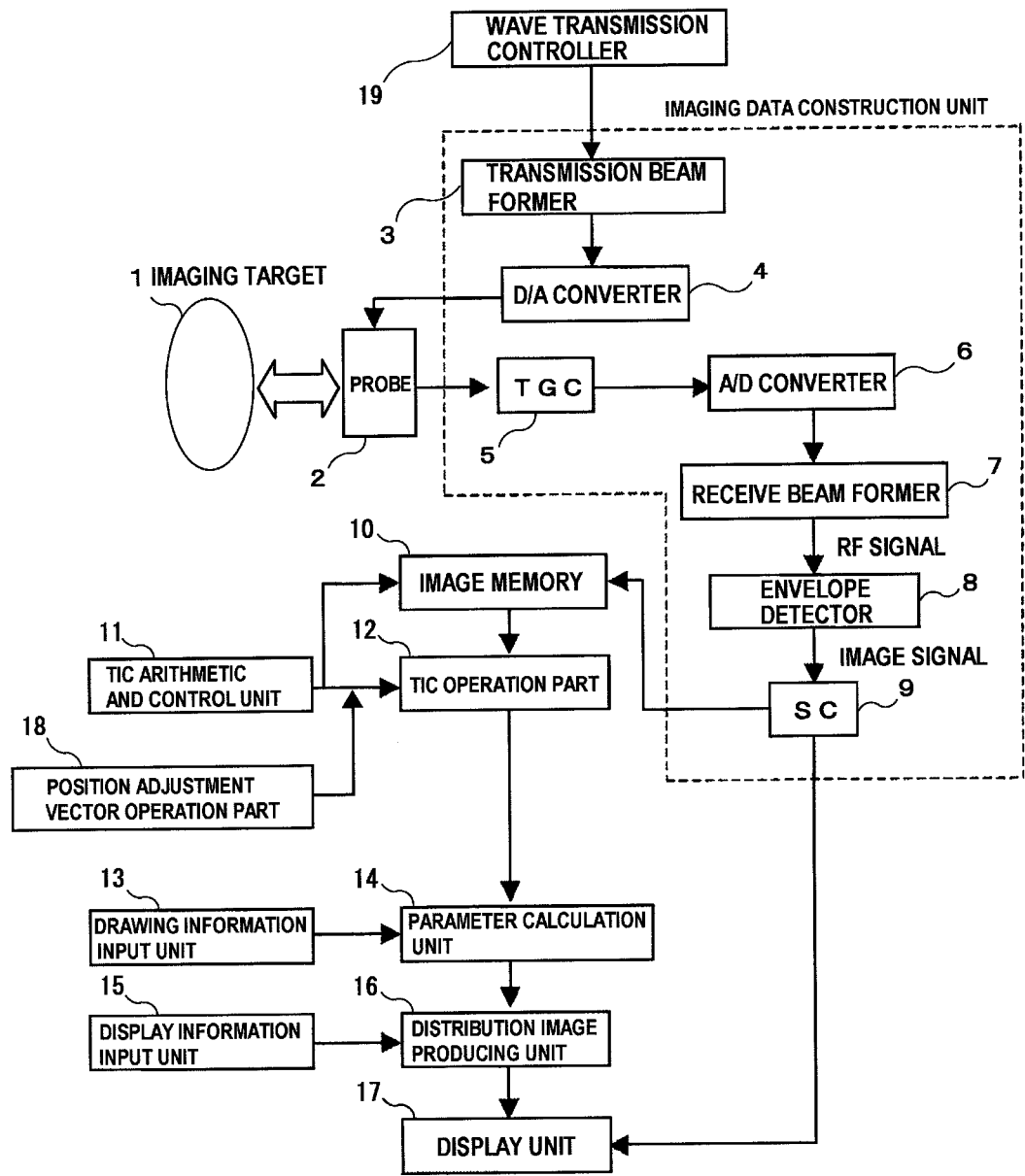
FIG. 22 is a block diagram showing a configuration example where the position adjustment vector operation part is provided in addition to the device configuration of the second embodiment.

In order to reduce influence of displacement of the imaging target, which occurs upon generating the TIC, the position adjustment vector operation part 18 is provided as shown in FIG. 22, in addition to the device configuration shown in FIG. 19.

Figure 23:
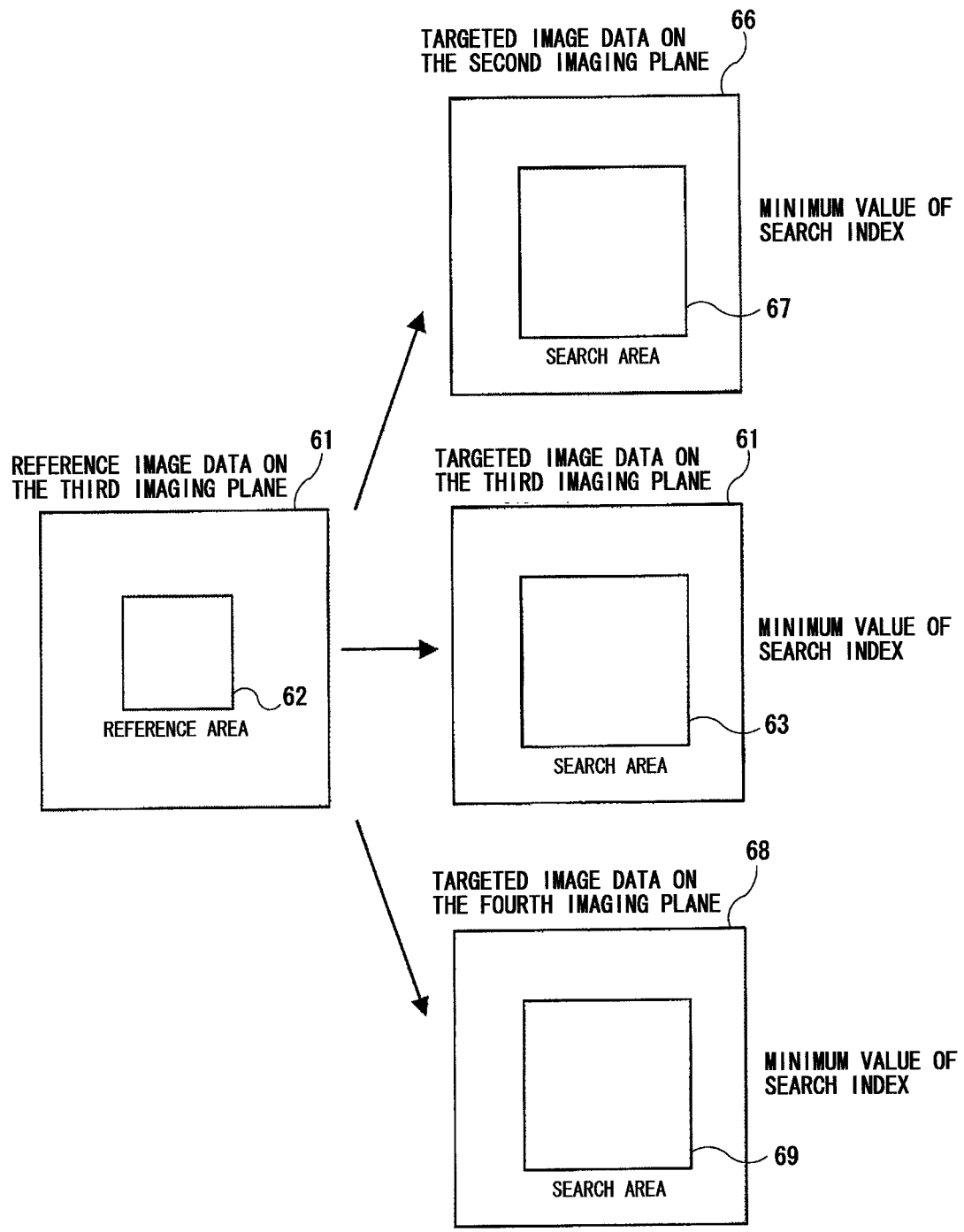
FIG. 23 illustrates the position adjustment process according to the second embodiment.

A method of position adjustment according to the position adjustment vector operation part 18 is the same as the method described in the first embodiment. However, a search area is expanded three-dimensionally. Now focusing attention on the third imaging plane as shown in FIG. 20 and FIG. 21, an explanation will be made as to the case where a difference absolute value is used as an index for searching. Firstly, as shown in FIG. 23, a search area 63 of image data 61 being a target for position adjustment in the same imaging plane, i.e., the third imaging plane, is searched to find an area whose difference absolute value relative to the reference area 62 is a minimum. Subsequently, the image data 66 and the image data 68 are selected, which are acquired in the same time phase (the same scan) with the image data searched previously, respectively from the image data items associated with the contiguous second imaging plane and the fourth imaging plane, then setting the search areas 67 and 69 to calculate a minimum value of search index for each. The minimum values calculated on each of the imaging planes are compared, and the area having the smallest value is considered to be a matching area, thereby fixing a position adjustment vector.

The smoothing method is also applicable in the same manner as the first embodiment, which performs smoothing by comparing the TIC of a focused pixel with the TICs of surrounding pixels. The pixel used for the adjustment may be selected from the same imaging plane, or it may be selected from other contiguous imaging plane. A method for selecting the intensity per time unit is the same as the method described in the first embodiment.

The color maps three-dimensionally produced may be displayed side by side, or displayed in superimposed manner with a CT image, an MR image, or a PET image.

It is to be noted that the aforementioned image display apparatus implements a technique for acquiring intensity change on the image data per pixel in the form of TIC, and converting the parameter values being calculated from the TIC into color maps. Therefore, an applicable scope of the present technique is not limited to an ultrasonic image, but covers entire digital image data, such as an MR image, a CT image, and a PET image.

Features of the image display apparatus according to the present invention are as the following.

The image display apparatus includes, a probe for transmitting and receiving ultrasonic waves to and from an imaging target, an image data construction unit for constructing image data based on signals acquired by the probe, an image memory for storing the image data, a TIC arithmetic and control unit for controlling acquisition of the image data and generation of a TIC, a TIC operation part for generating the TIC from an intensity value on the image data, a parameter calculation unit for calculating from the TIC a value of evaluation index (parameter) required for producing an image, a distribution image producing unit for producing based on the parameter value, a two-dimensional color map on which blood flow dynamics are reflected, a display unit for displaying the color map that is produced in the distribution image producing unit, and a display information input unit for changing a display mode of the image being displayed.

The image display apparatus further includes a TIC arithmetic and control unit for setting a region of interest on the image data being stored, and setting a sampling interval, and the TIC arithmetic and control unit is characterized in performing control relating to steps of storing image data and processing for generating the TIC.

The image display apparatus is characterized in that the TIC generated in the TIC operation part is smoothed by an averaging process in a direction of time, where the number of the measurement points (sampling points) is maintained.

The image display apparatus is characterized in that the process for generating the TIC in the TIC operation part is executed as to the entire pixels of the image data being stored, or as to each area being predetermined.

The image display apparatus is characterized in that the TIC operation part simplifies by using a predetermined function, variation of the intensity caused by perfusion of the contrast agent, and calculates a peculiar measurement point of the TIC.

The image display apparatus is characterized in that the function set in the TIC operation part represents a constant value from a measurement start to a first point, a linear increase from the first point to a second point, a constant value from the second point to a third point, and a linear decrease from the third point, or represents a constant value from the measurement start to the first point, and from the first point, the function corresponding to a function $y=A(1-e^{-\beta t})$ representing a TIC generally known, assuming that balanced intensity is A, time is t, and variation of the intensity along with the inflow of the contrast agent is $\beta$.

The image display apparatus further includes a drawing information input unit for inputting drawing information required by the operator, and it is characterized in that a parameter value calculated from the TIC by the parameter calculation unit reflects the drawing information.

The image display apparatus is characterized in that the drawing information input unit allows the operator to perform inputting, on the basis of the drawing information displayed in the navigation screen on the display unit, and the TIC on which the information indicating the drawing information is reflected.

The image display apparatus is characterized in that setting the drawing information in advance eliminates inputting of the drawing information in the drawing information input unit.

The image display apparatus is characterized in that the navigation screen or the drawing information displayed by an image information controller is freely editable by the operator, such as addition and deletion of an item, and modification of a text.

The image display apparatus is characterized in that the display unit displays a static image or a moving image of the image data being acquired, and the TICs of regions of interest being set by the operator on the static image or on the moving image are displayed side by side or displayed in a superimposed manner, and as for the TICs being displayed in superimposed manner, the operator designates the region of interest or the TIC.

The image display apparatus is characterized in that information inputted in the drawing information input unit relates to blood flow dynamics, such as a contrast agent inflow start time, a balanced intensity arrival time, a contrast agent disappearance start time, a contrast agent duration, a preset threshold arrival time, an intensity increase rate or a decrease rate, intensity of balanced state, and a total flow amount.

The image display apparatus is characterized in that the parameter value calculated in the parameter calculation unit reflects the information inputted in the drawing information input unit, and the parameter value is calculated from the TIC indicating variation of the intensity along with perfusion of the contrast agent.

The image display apparatus is characterized in that an image produced by the distribution image producing unit is a color map that is color coded according to the value calculated by the parameter calculation unit.

The image display apparatus is characterized in that as for a display mode of the color map on the display unit, the operator is allowed to freely edit a combination, arrangement, and a size of the information items to be displayed, among the drawing information, the static image or moving image of the image data being acquired, the TIC of the region of interest designated by the operator, and the color map.

The image display apparatus is characterized in that the color map produced by the distribution image producing unit is allowed to optimize a color range within a range of the region of interest that is set by the operator on the color map.

The image display apparatus is characterized in that in the color map produced by the distribution image producing unit, a color range being focused is designated by using arrows displayed on a color bar indicating a relationship between the parameter values and the colors belonging to the color map, thereby reproducing the color map within the area included in the designated range on the color map, and enhancing the color range.

The image display apparatus is characterized in that in the color map produced by the distribution image producing unit, a reference area is designated on the color map, thereby reproducing the color map assuming the reference area as a reference.

The image display apparatus is characterized in that as for the color map produced by the distribution image producing unit, a range of parameter value displayed on the color map is allowed to be limited by the TIC representing the focused area.

The image display apparatus is characterized in that the display information input unit accepts overall display mode information inputted by the operator, such as a combination to be displayed, a size to be displayed, a combination of a reconstructed images and a background image, from information such as the TIC being generated, image data being stored, and the color map being produced, for instance, and reflects the accepted information on the distribution image producing unit or the display unit.

The image display apparatus is characterized in that as for the color map produced by the distribution image producing unit, a color map included in the range of the parameter value being focused, and a color map not included in the range of the parameter value being focused are produced, an area being focused or an area not included in the focused area is distinguished according to color shading or color distribution, and then both images are superimposed one on another.

The image display apparatus is characterized in that the color map produced by the distribution image producing unit is displayed, in combination with any of the followings as a background image; a color map made up of different drawing information, an ultrasonic image, an MR image, a CT image, a PET image, and another image of the same imaging target.

The image display apparatus is characterized in that as for the color map produced by the distribution image producing unit, an image obtained by subjecting the image data being acquired to imaging process such as vessel enhancement is set as a background image, and the color map is displayed in such a manner as superimposed thereon.

The image display apparatus is characterized in that the information the operator inputs in the drawing information input unit and in the display information input unit may be predetermined prior to an operation and the settings are stored to be reflected for the next time.

The image display apparatus is characterized in that the drawing information displayed on the navigation screen in the drawing information input unit may be ranked in the order from the highest selecting frequency by the operator in the past, from the most significant information in tumor diagnosis, or the like, and the operator is allowed to freely sort the information for display.

The image display apparatus includes a probe for transmitting and receiving ultrasonic waves to and from an imaging target, an image data construction unit for constructing image data based on signals acquired by the probe, a wave transmission controller for controlling a wave transmission sequence, an image memory for storing the image data, a TIC arithmetic and control unit for controlling generation of a TIC, a TIC operation part for generating the TIC from intensity value of the image data, a drawing information input unit for inputting drawing information required by the operator, a parameter calculation unit for calculating from the TIC, a parameter value associated with the drawing information, a distribution image producing unit for producing from the parameter value, a three-dimensional color map on which blood flow dynamics are reflected, a display unit for displaying the three-dimensional color map produced by the distribution image producing unit, a display information input unit for changing a display mode of the image being displayed.

The image display apparatus is characterized in that the probe may be one-dimensional array type probe on which a drive unit such as a motor is provided, or a two-dimensional type probe, and the probe is capable of acquiring image data items on multiple different imaging planes.

The image display apparatus is characterized in that the 3-D color map produced in the distribution image producing unit is made up of three-dimensionally combined two-dimensional color maps, each two-dimensional color maps being produced on different imaging planes.

The image display apparatus is characterized in that in generating the TIC by the TIC operation part, the position adjustment vector operation part adjusts displacement in the space on the imaging target.

The image display apparatus is characterized in that the color map produced by the distribution image producing unit is displayed, in combination with any of the followings as a background image; a color map made up of different drawing information, an ultrasonic image, an MR image, a CT image, a PET image, and another image of the same imaging target.

EXPLANATION OF REFERENCES

1 . . . IMAGING TARGET, 2 . . . PROBE, 3 . . . TRANSMISSION BEAM FORMER, 4 . . . D/A CONVERTER, 5 . . . TGC (TIME-GAIN CONTROLLER), 6 . . . A/D CONVERTER, 7 . . . RECEIVE BEAM FORMER, 8 . . . ENVELOPE DETECTOR, 9 . . . SC (SCAN CONVERTER), 10 . . . IMAGE MEMORY, 11 . . . TIC (TIME INTENSITY CURVE) ARITHMETIC AND CONTROL UNIT, 12 . . . TIC OPERATION PART, 13 . . . DRAWING INFORMATION INPUT UNIT, 14 . . . PARAMETER VALUE CALCULATION UNIT, 15 . . . DISPLAY INFORMATION INPUT UNIT, 16 . . . DISTRIBUTION IMAGE PRODUCING UNIT, 17 . . . DISPLAY UNIT, 18 . . . POSITION ADJUSTMENT VECTOR OPERATION PART, 19 . . . WAVE TRANSMISSION CONTROLLER, 41 . . . DISPLAY SCREEN, 51 . . . NAVIGATION SCREEN, 211 . . . STRUCTURAL OBJECT, 212 . . . TIC ACQUISITION POSITION

What is claimed is:

1. An ultrasonic diagnostic apparatus comprising:
a probe which transmits and receives ultrasonic waves to and from an imaging target;
an image data constructor configured to construct image data based on signals received by the probe;
a time-intensity curve calculator configured to generate a time-intensity curve from intensity values of a pixel of the image data at plural points of time;
a distribution image producer configured to produce a distribution image of blood flow dynamics from a parameter value obtained from the time-intensity curve, the parameter being predetermined; and
a display which displays the distribution image of the blood flow dynamics,
wherein the time-intensity curve calculator: calculates a difference value between pixels, respectively of the image data being acquired at different points of time; calculates a total sum of the difference value of each pixel; and decides a starting point of time of generating the time-intensity curve based on the total sum of the difference value.

2. The ultrasonic diagnostic apparatus according to claim 1, further comprising;
a position adjustment vector operator configured to perform an arithmetical operation to obtain a position adjustment vector of the imaging target in a space,
wherein the time-intensity curve calculator adjusts a spatial position of the imaging target by using the position adjustment vector, and generates the time-intensity curve at an adjusted spatial position of the imaging target.

3. The ultrasonic diagnostic apparatus according to claim 1, further comprising:
a drawing information input unit configured to accept an input of drawing information by an operator, and
a parameter calculator configured to calculate from the time-intensity curve as the parameter value, a value of the parameter being predetermined in association with the drawing information accepted by the drawing information input unit.

4. The ultrasonic diagnostic apparatus according to claim 3, wherein the drawing information corresponds to at least one of a plurality of information items relating to the blood flow dynamics, the plurality of information items including:
a contrast agent inflow start time;
a balanced intensity arrival time;
a contrast agent disappearance start time;
a contrast agent duration;
a preset threshold arrival time;
an intensity increase rate, an intensity decrease rate;
intensity of balanced state; and
a total flow amount.

5. The ultrasonic diagnostic apparatus according to claim 3, wherein the parameter value calculated by the parameter calculator corresponds to a value calculated from the time-intensity curve indicating intensity change along with perfusion of the contrast agent administered to the imaging target.

6. The ultrasonic diagnostic apparatus according to claim 1, wherein the distribution image producer is configured to produce either of a two-dimensional color map image and a three-dimensional color map image, being color coded according to the parameter value.

7. The ultrasonic diagnostic apparatus according to claim 1, further comprising:
a display information input unit configured to accept a setting by an operator as to a display mode,
wherein the distribution image producer produces an image which displays at least one of plurality of parameters in the display mode accepted by the display information input unit, the plurality of parameters including:
the drawing information;
a static image or a moving image of the image data being acquired;
a time-intensity curve of a region of interest; and
a distribution image of the blood flow dynamics being color coded according to the parameter value.

8. A method of producing a distribution image of blood flow dynamics, the method comprising the steps of:
transmitting and receiving ultrasonic waves to and from a target for contrast imaging via a probe, assuming a test subject who is administered a contrast agent as an imaging target;
constructing image data based on signals received by the probe;
generating a time-intensity curve from an intensity values of a pixel of the image data at plural points of time;
calculating a parameter value from the time-intensity curve to produce the distribution image of the blood flow dynamics, the parameter value being predetermined;
producing the distribution image of the blood flow dynamics from the parameter value;
calculating a difference value between pixels, respectively of the image data being acquired at different points of time;
calculating a total sum of the difference value of each pixel; and
deciding a starting point of time of generating the time-intensity curve based on the total sum of the difference value.

9. The method of producing a distribution image of blood flow dynamics according to claim 8, further comprising the step of:
performing an arithmetical operation to obtain a vector for adjusting a position of the imaging target in a space,
wherein the step of generating the time-intensity curve adjusts the position of the imaging target according to the vector for adjusting the position, and generates the time-intensity curve from the image data of the imaging target as to which the position has been adjusted.

10. The method of producing a distribution image of blood flow dynamics according to claim 8, further comprising the step of:
accepting an input of drawing information by an operator,
wherein the step of calculating the parameter value calculates from the time-intensity curve as the parameter value, a value of the parameter value being predetermined in association with the drawing information being accepted.

11. The method of producing a distribution image of blood flow dynamics according to claim 10,
wherein the drawing information corresponds to at least one of a plurality of information items relating to the blood flow dynamics, the plurality of information items including:
a contrast agent inflow start time;
a balanced intensity arrival time;
a contrast agent disappearance start time;
a contrast agent duration;
a preset threshold arrival time;
an intensity increase rate;
an intensity decrease rate, intensity of balanced state; and
a total flow amount.

12. The method of producing a distribution image of blood flow dynamics according to claim 10,
wherein the parameter value calculated by the step of calculating the parameter value is calculated from the time-intensity curve indicating intensity change along with perfusion of the contrast agent administered to the imaging target.

13. The method of producing a distribution image of blood flow dynamics according to claim 8,
wherein the step of producing the distribution image of the blood flow dynamics produces either of a two-dimensional color map image and a three-dimensional color map image, being color coded according to the parameter value.

14. The method of producing a distribution image of blood flow dynamics according to claim 13,
  wherein the color map image is accompanied with a color bar representing an association between a color and the parameter value, and an operation by the operator for shifting a position of an arrow attached to the color bar modifies settings of at least either one of a range of the parameter values and a color range, to be displayed on the color map image.

15. The method of producing a distribution image of blood flow dynamics according to claim 9,
  wherein the step of generating the time-intensity curve generates the time-intensity curve as to an identical portion of the imaging target, from the image data in the space of the imaging target, the position of the image data having been adjusted by the vector for adjusting the position.

16. The ultrasonic diagnostic apparatus according to claim 1, wherein the time-intensity curve calculator subtracts an initial value of intensity at starting points of the time-intensity curve from intensity value of the time-intensity curve at each point of time, so as to make the value of intensity at the starting points zero.

17. The method of producing a distribution image of blood flow dynamics according to claim 8, further comprising:
  subtracting an initial value of intensity at starting points of the time-intensity curve from intensity value of the time-intensity curve at each point of time, so as to make the value of intensity at the starting points zero.

\* \* \* \* \*